United States Patent
Goto

(10) Patent No.: US 7,862,603 B2
(45) Date of Patent: Jan. 4, 2011

(54) STENT DELIVERY SYSTEM

(75) Inventor: Hiroaki Goto, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 254 days.

(21) Appl. No.: 11/875,462

(22) Filed: Oct. 19, 2007

(65) Prior Publication Data

US 2008/0103581 A1    May 1, 2008

(30) Foreign Application Priority Data

Oct. 19, 2006    (JP) .............................. 2006-284996

(51) Int. Cl.
  *A61F 2/06*    (2006.01)
(52) U.S. Cl. ..................... 623/1.11; 606/108
(58) Field of Classification Search ....... 623/1.11–1.15, 623/1.42; 606/108; 600/101
  See application file for complete search history.

(56) References Cited

U.S. PATENT DOCUMENTS

| 5,603,698 | A |   | 2/1997  | Roberts et al. |         |
|-----------|---|---|---------|----------------|---------|
| 5,817,102 | A | * | 10/1998 | Johnson et al. | 606/108 |
| 6,136,006 | A | * | 10/2000 | Johnson et al. | 606/108 |
| 6,146,389 | A | * | 11/2000 | Geitz          | 606/108 |
| 6,162,231 | A | * | 12/2000 | Mikus et al.   | 606/108 |
| 6,517,569 | B2| * | 2/2003  | Mikus et al.   | 623/1.11|
| 6,576,005 | B1| * | 6/2003  | Geitz          | 623/1.11|
| 2002/0183827 | A1 | * | 12/2002 | Derus et al. | 623/1.12 |
| 2004/0092794 | A1 | * | 5/2004  | Chin et al.  | 600/146  |
| 2005/0033403 | A1 |   | 2/2005  | Ward et al.  |          |
| 2007/0293929 | A1 | * | 12/2007 | Aoba et al.  | 623/1.11 |
| 2009/0182410 | A1 | * | 7/2009  | Case et al.  | 623/1.11 |

FOREIGN PATENT DOCUMENTS

| EP | 1 656 963 A1 | 5/2006 |
| JP | H10-507090 | 7/1998 |
| JP | 2006-516200 | 6/2006 |
| WO | WO 96/12436 | 5/1996 |
| WO | WO 02/03889 A2 | 1/2002 |
| WO | WO 2004/030571 A2 | 4/2004 |
| WO | WO 2006/124822 A1 | 11/2006 |
| WO | WO 2007/048437 A1 | 5/2007 |
| WO | WO 2007/117930 A2 | 10/2007 |

* cited by examiner

*Primary Examiner*—Suzette J Gherbi
(74) *Attorney, Agent, or Firm*—Scully, Scott, Murphy & Presser, P.C.

(57) ABSTRACT

A stent delivery system 1 for supplying a stent to a body cavity which includes an endoscope 6 that has an insertion portion 5 with a curvature portion 3 disposed at the distal end thereof, a sheath 7 that is disposed with the insertion portion 5 inserted in the inside thereof and a stent 2 placed on the outer surface of the distal end side thereof; and a regulating portion 8 that regulates the relative movement of the stent 2 to the proximal end side of the sheath 7, with the sheath 7 formed of a length that allows the distal end of the insertion portion 5 that is inserted in the sheath 7 to protrude from the distal end of the sheath 7. In accordance with the present invention, it is possible to provide a stent delivery system that can place a stent by endoscope observation without the need of excessive diametrical contraction or additional expansion of the stent.

17 Claims, 15 Drawing Sheets

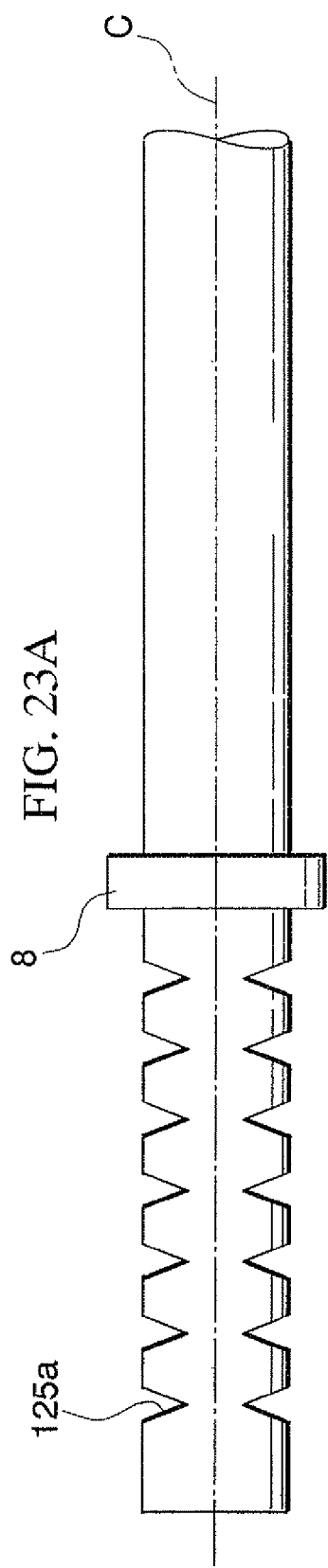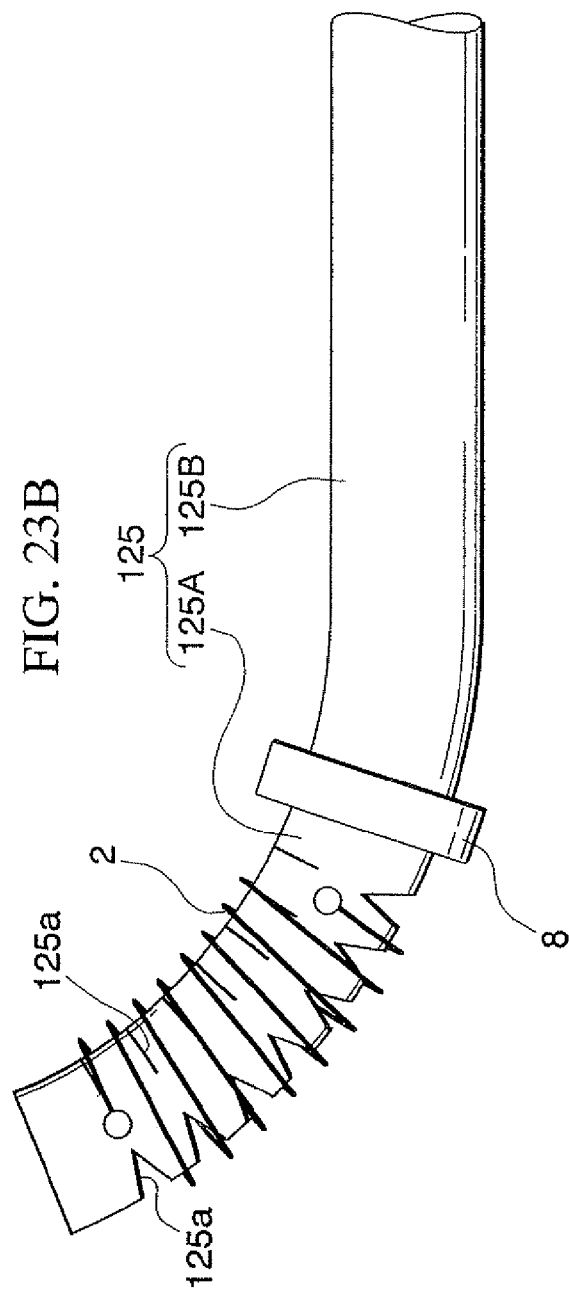

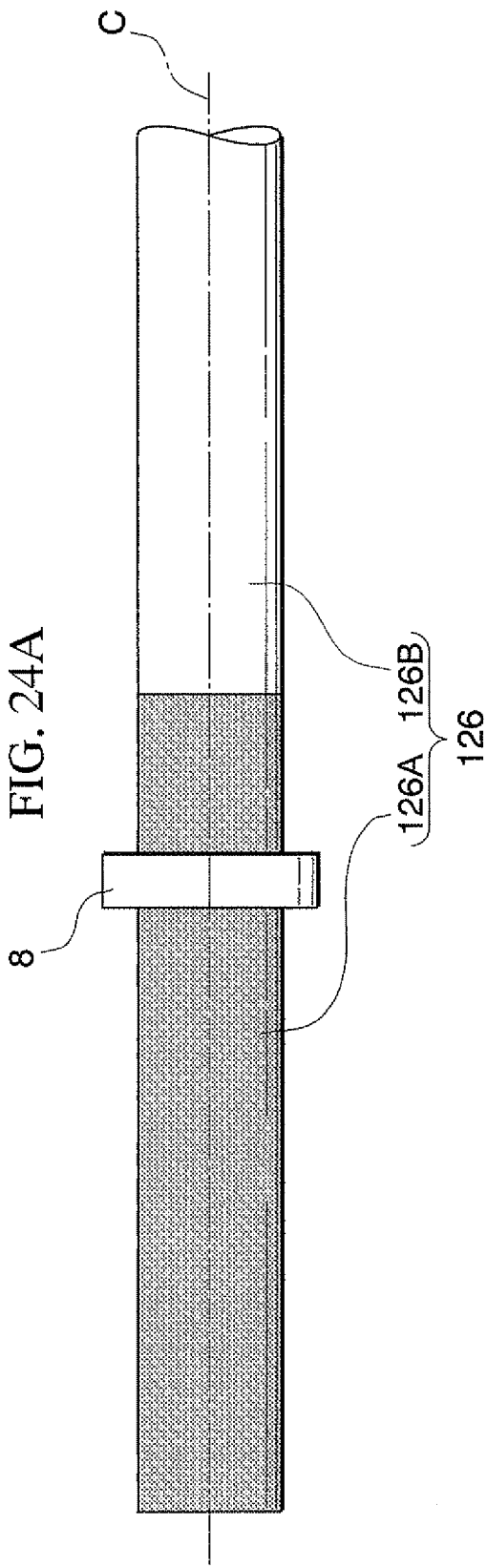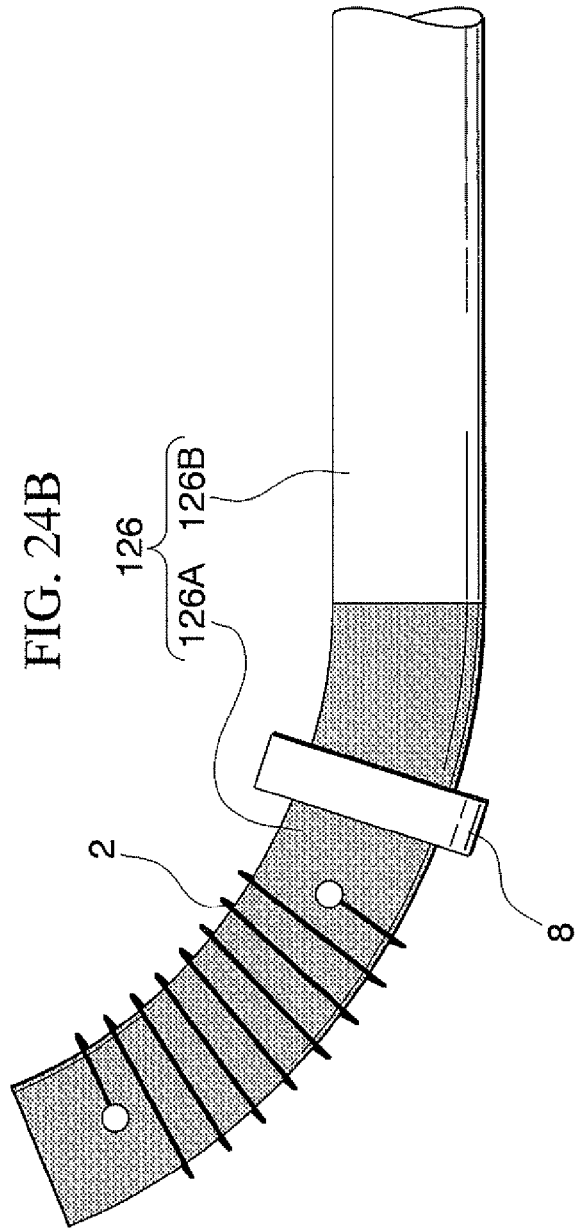

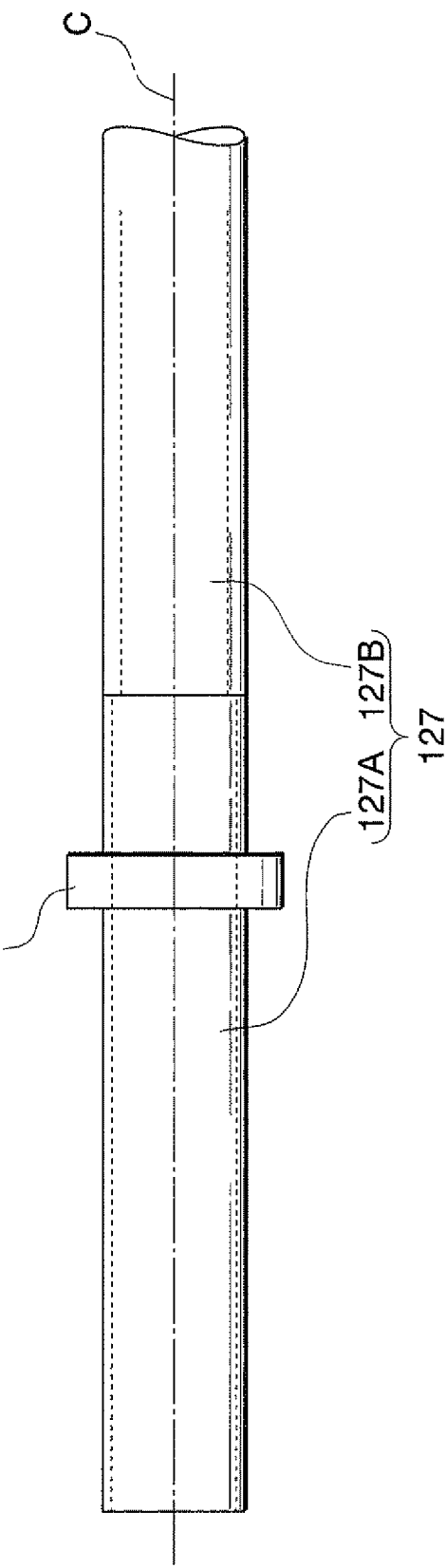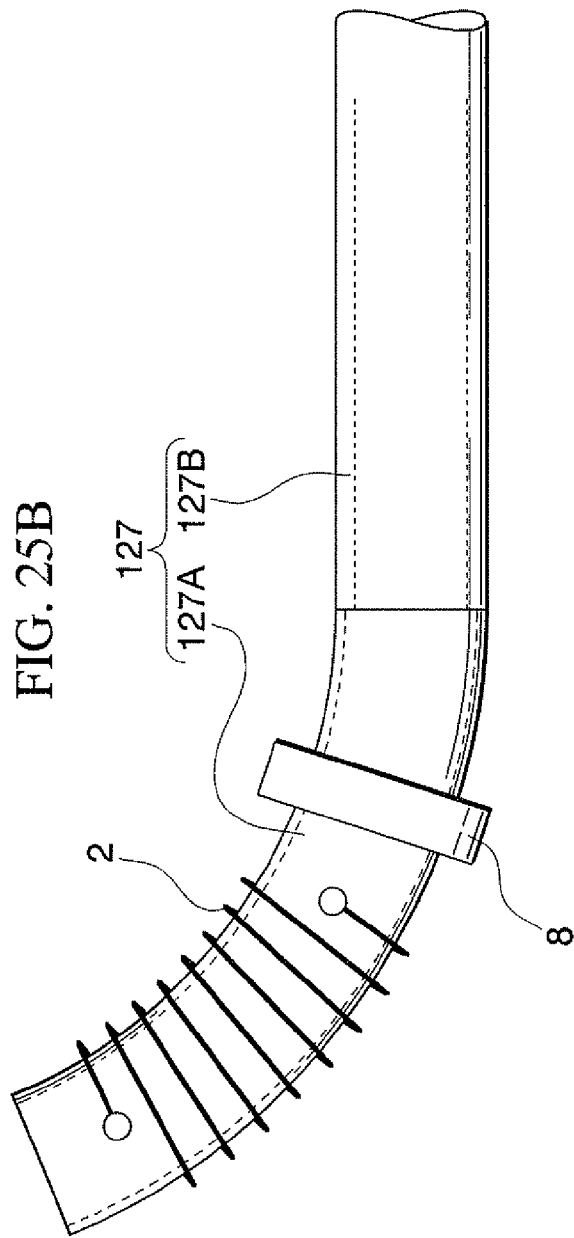

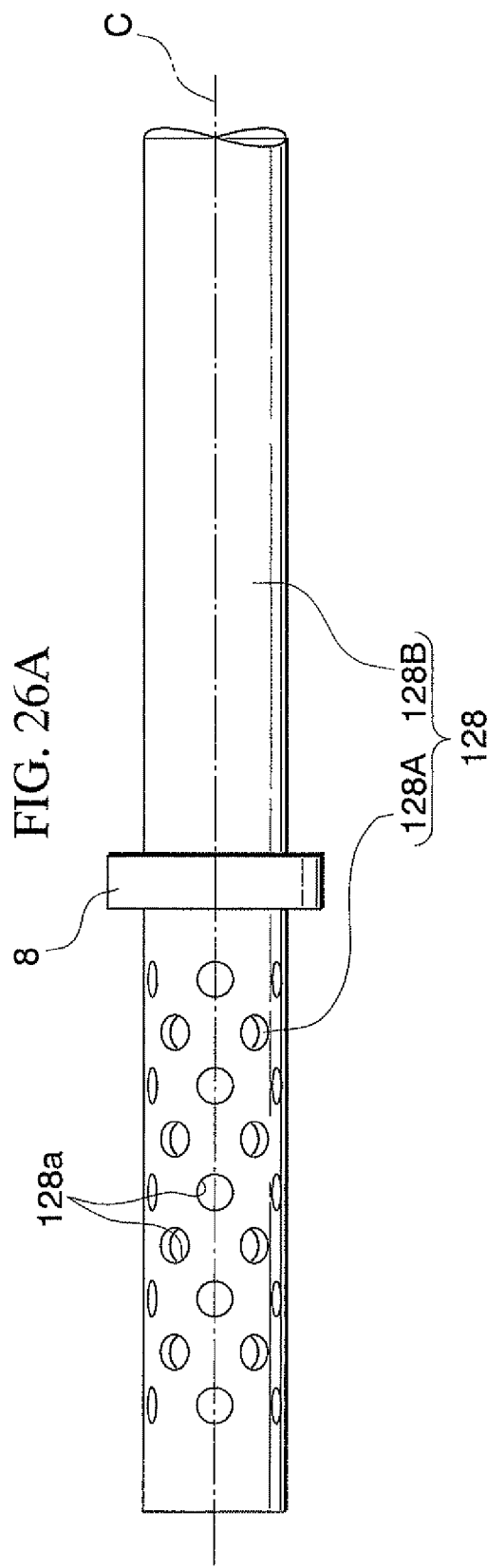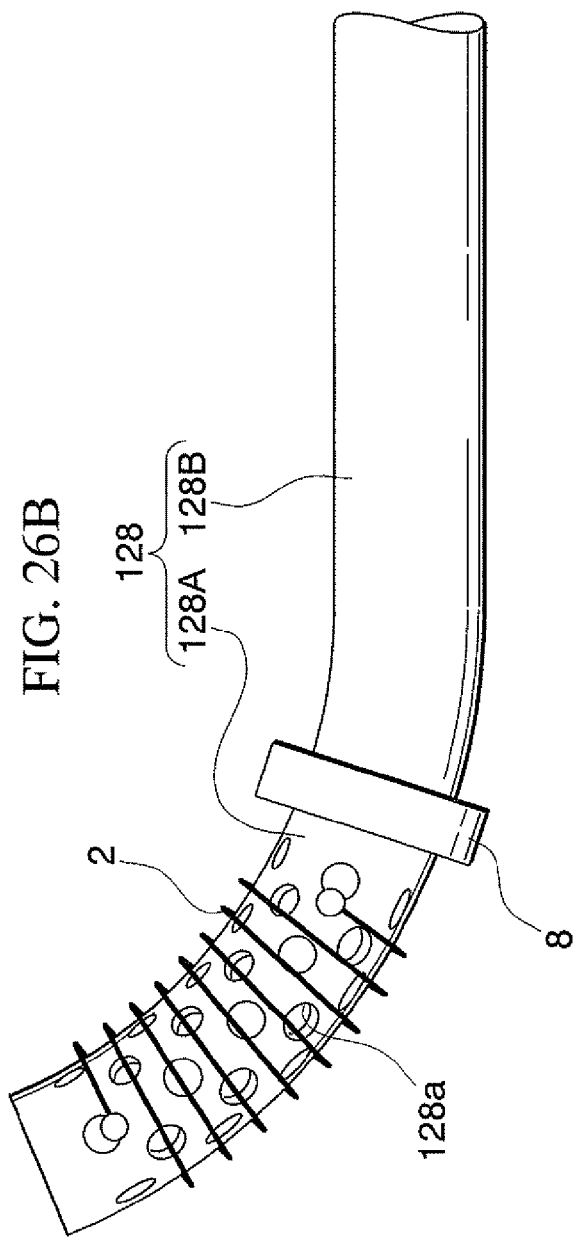

STENT DELIVERY SYSTEM

BACKGROUND OF THE INVENTION

1. Field of the Invention

The present invention relates to a stent delivery system.

Priority is claimed on Japanese Patent Application No. 2006-284996, filed Oct. 19, 2006, the content of which is incorporated herein by reference.

2. Description of Related Art

When inserting a stent into a body cavity endoscopically, there are times when the stent is placed by contracting the outer diameter of the stent and inserting it in a channel of the endoscope. On the other hand, when placing a stent without insertion in a channel of an endoscope, the stent is inserted via methods shown for example in Patent Documents 1 and 2 while confirming the position of the stent using an X-ray fluoroscope.

Patent Document 1: Published Japanese translation No. 2006-516200 of the PCT International Publication Patent Document 2: Published Japanese translation No. H10-507090 of the PCT International Publication

SUMMARY OF THE INVENTION

A first aspect of the stent delivery system in accordance with the present invention is a stent delivery system for supplying a stent to a body cavity which includes: an endoscope that has an insertion portion that is inserted into a body cavity; a sheath that is disposed with the insertion portion inserted in the inside thereof and the stent placed on the outer surface of the distal end side thereof; and a regulating portion that regulates the relative movement of the stent to the proximal end side of the sheath; in which the sheath is formed of a length that allows the distal end of the insertion portion that is inserted in the sheath to protrude from the distal end of the sheath.

Also, a second aspect of the stent delivery system in accordance with the present invention is the aforementioned stent delivery system, in which an indictor portion that shows the state of alignment of the distal end of the sheath and the distal end of the insertion portion is provided in the insertion portion.

Also, a third aspect of the stent delivery system in accordance with the present invention is the aforementioned stent delivery system, which is provided with an outer sheath that is disposed in a manner to freely extend and retract with respect to the sheath and additionally covers the outer side of the stent in the state of the stent is placed on the sheath.

Also, a forth aspect of the stent delivery system in accordance with the present invention is the aforementioned stent delivery system, in which the regulating portion is provided with a line, with at least a portion of the line being connected to the distal end side of the sheath in the vicinity of the stent in the state of being in contact with the stent.

Also, a fifth aspect of the stent delivery system in accordance with the present invention is the aforementioned stent delivery system, in which the sheath includes a large diameter portion that is covered by the stent and a narrow diameter portion having a smaller diameter than the large diameter portion and disposed at the distal end of the large diameter portion.

Also, a sixth aspect of the stent delivery system in accordance with the present invention is the aforementioned stent delivery system, in which a window portion that enables visual recognition of the outside of the sheath by the endoscope from the inside thereof is provided on the distal end side of the sheath.

Also, a seventh aspect of the stent delivery system in accordance with the present invention is the aforementioned stent delivery system, in which the window portion is preferably constituted by the distal end side of the sheath is formed with a transparent material.

Also, an eighth aspect of the stent delivery system in accordance with the present invention is the aforementioned stent delivery system, in which a curvature portion is disposed on the distal end side of the insertion portion, and the sheath is formed of a length that allows the curvature portion to protrude from the distal end thereof.

Also, a ninth aspect of the stent delivery system in accordance with the present invention is the aforementioned stent delivery system, in which a sheath large diameter portion that is larger than the outer diameter of the stent is provided further to the proximal end side of the sheath than the position where the stent is placed, with the sheath large diameter portion serving as the regulating portion.

Also, a tenth aspect of the stent delivery system in accordance with the present invention is the aforementioned stent delivery system, in which at least a portion of the distal end side of the sheath curves in compliance with the curvature of the curvature portion.

Also, an eleventh aspect of the stent delivery system in accordance with the present invention is the aforementioned stent delivery system, in which the inner diameter of at least a portion of the narrow diameter portion is formed approximately the same as the outer diameter of the endoscope or smaller than the outer diameter of the endoscope; and a slit is provided in a portion of the narrow diameter portion.

Also, a twelfth aspect of the stent delivery system in accordance with the present invention is the aforementioned stent delivery system, in which a flexible portion having a member that is more flexible than the member that constitutes the sheath is disposed at the distal end of the sheath.

Also, a thirteenth aspect of the stent delivery system in accordance with the present invention is the aforementioned stent delivery system, in which the window portion is disposed at a position of the sheath where at least a portion of the most distal end of the stent that is disposed by placement on the sheath is visually recognizable.

Also, a fourteenth aspect of the stent delivery system in accordance with the present invention is a stent delivery system for supplying a stent to a body cavity, which includes: an endoscope that has in insertion portion that is inserted into a body cavity in which the stent is disposed by being placed on the outer surface of the distal end side thereof, and a regulating portion that regulates the relative movement of the stent to the proximal end side of the insertion portion.

Also, a fifteenth aspect of the stent delivery system in accordance with the present invention is the aforementioned stent delivery system, in which a curvature portion is disposed on the distal end side of the insertion portion, and the stent is formed to be capable of curving in compliance with the curvature of the curvature portion.

Also, a sixteenth aspect of the stent delivery system in accordance with the present invention is the aforementioned stent delivery system, which is provided with a diameter adjustment portion that makes the outer diameter of at least the distal end side of the stent that is placed on the insertion portion gradually approach the outer diameter of the insertion portion.

Also, a seventeenth aspect of the stent delivery system in accordance with the present invention is the aforementioned stent delivery system, in which a small diameter portion in which the outer diameter of at least a portion thereof is smaller than the proximal end side of the insertion portion is disposed at the distal end of the insertion portion.

BRIEF DESCRIPTION OF THE DRAWINGS

FIG. 23A is a main portion schematic drawing showing a modification example of the stent delivery system in accordance with the first embodiment of the present invention.

FIG. 23B is a main portion schematic drawing showing a modification example of the stent delivery system in accordance with the first embodiment of the present invention.

FIG. 24A is a main portion schematic drawing showing a modification example of the stent delivery system in accordance with the first embodiment of the present invention.

FIG. 24B is an explanatory drawing of a bent state showing a modification example of the stent delivery system in accordance with the first embodiment of the present invention.

FIG. 25A is a main portion schematic drawing showing a modification example of the stent delivery system in accordance with the first embodiment of the present invention.

FIG. 25B is an explanatory drawing of a bent state showing a modification example of the stent delivery system in accordance with the first embodiment of the present invention.

FIG. 26A is a main portion schematic drawing showing a modification example of the stent delivery system in accordance with the first embodiment of the present invention.

FIG. 26B is an explanatory drawing of a bent state showing a modification example of the stent delivery system in accordance with the first embodiment of the present invention.

DETAILED DESCRIPTION OF THE INVENTION

A first embodiment in accordance with the present invention shall be described with reference to FIGS. 1 to 3B.

Figure 1:
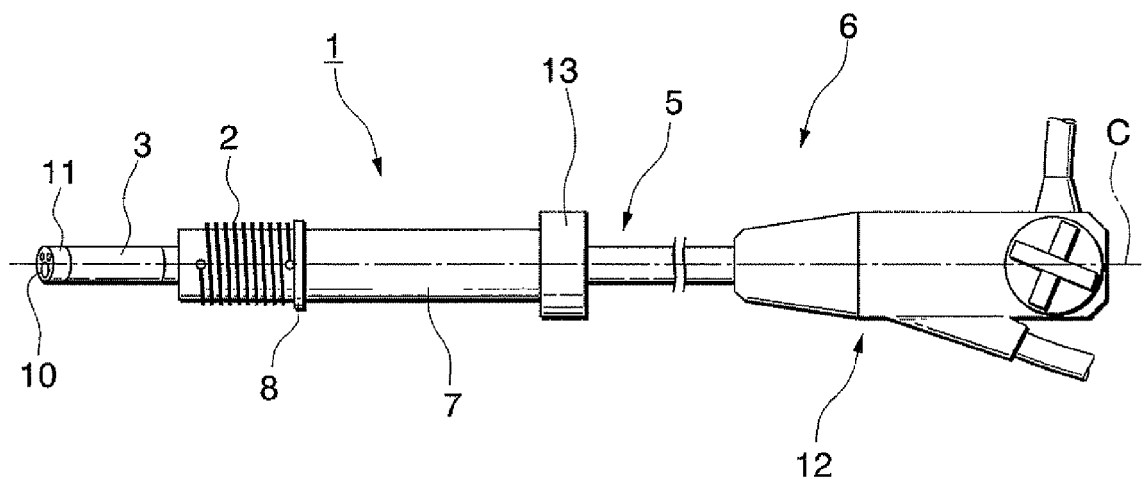
FIG. 1 is an overall schematic drawing showing the stent delivery system in accordance with the first embodiment of the present invention.
Figure 2:
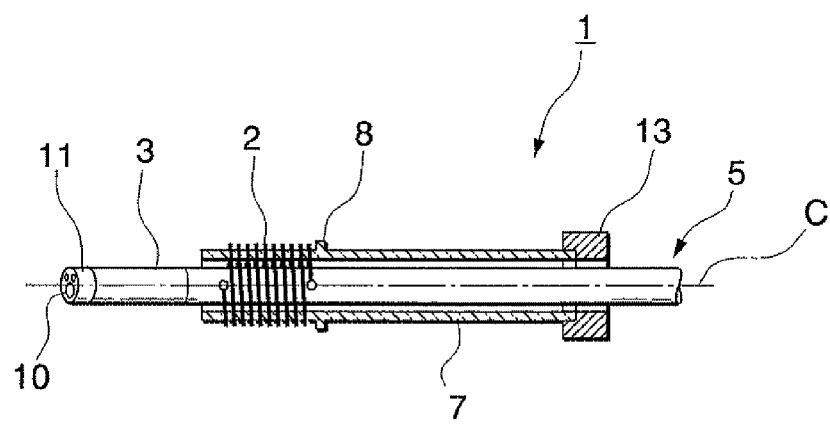
FIG. 2 is a main portion sectional view showing the stent delivery system in accordance with the first embodiment of the present invention.

A stent delivery system 1 in accordance with the present invention is a stent delivery system for supplying a stent 2 to a constricted portion inside a body cavity not shown. As shown in FIG. 1 and FIG. 2, the stent delivery system 1 includes an endoscope 6 that has an insertion portion 5 with a curvature portion 3 disposed on the distal end side, a sheath 7 that is disposed with the insertion portion 5 inserted in the inside thereof and the stent 2 placed on the outer surface of the distal end side thereof, and a regulating portion 8 that regulates the relative movement of the stent 2 to the proximal end side of the sheath 7.

The stent 2 is for example formed in a cylindrical shape by winding a wire in a loop shape. The stent 2 may be a self-expandable type or a non-self-expandable type.

At the distal end of the curvature portion 3, a distal end portion 11 having a lens 10 disposed therein is connected. The curvature portion 3 can direct the distal end portion 11 in various directions by operation of an operating portion 12 of the endoscope 6.

The sheath 7 has flexibility and is formed in a cylindrical shape. A grip portion 13 that protrudes in a radial direction outward is provided at the proximal end of the sheath 7. The sheath 7 is formed of a length such that, when the insertion portion 5 is inserted in the sheath 7, the curvature portion 3 of the insertion portion 5 can be protruded from the distal end of the sheath 7.

The regulating portion 8 is provided spaced by a predetermined distance from the distal end of the sheath 7 and protruding further outward from the outer surface of the sheath 7 in the radial direction than the outer diameter of the stent 2.

Figure 3A:
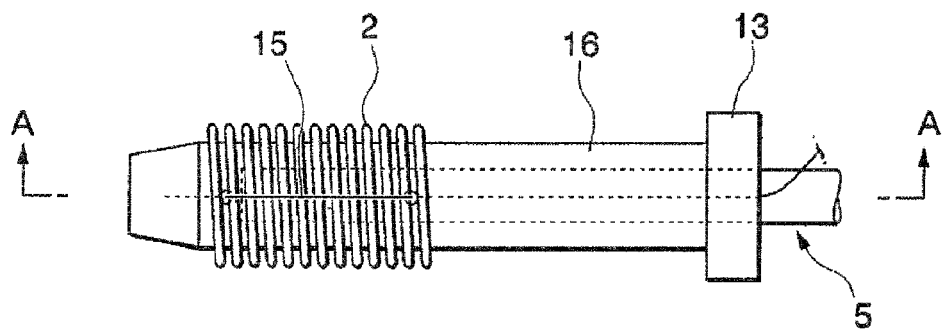
FIG. 3A is a main portion plan view showing a modification example of the stent delivery system in accordance with the first embodiment of the present invention.
Figure 3B:
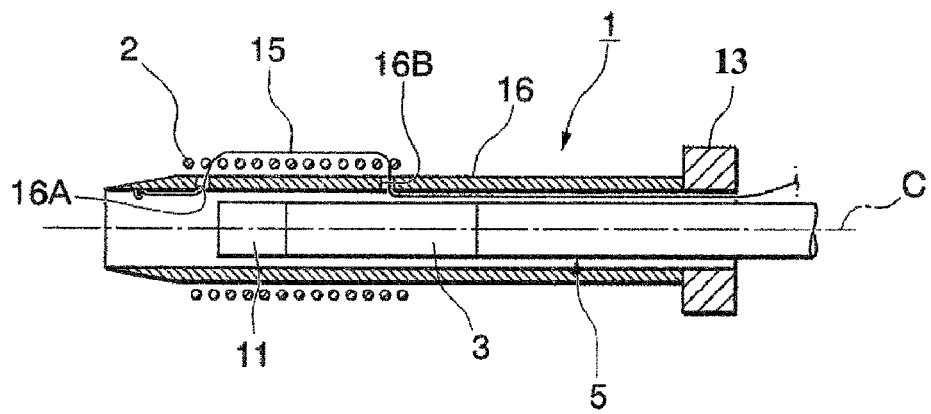
FIG. 3B is a sectional view along line A-A in FIG. 3A showing a modification example of the stent delivery system in accordance with the first embodiment of the present invention.

As shown in FIGS. 3A and 3B, regulating portion 15 may be constituted by a line. In this case, a first hole 16A is provided at the distal end side of the sheath 16 on which the stent 2 is mounted and a second hole 16B is provided by a predetermined distance away from the first hole 16A. The first hole 16A is located at a position that is covered by the distal end side of the stent 2, while the second hole 16B is covered by the proximal end side of the stent 2. One end of the regulating portion 15 is further to the distal end side of the sheath 7 than the distal end of the stent 2, being connected with the inside surface of the sheath 7 in the vicinity of the distal end opening thereof. The regulating portion 15 passes from there through the first hole 16A to once emerge on the outer surface of the stent 2. After being extended along the direction of the central axis line C of the stent 2, the regulating portion 15 is then passed through the second hold 16B to reemerge on the inner surface of the sheath 7 and is then extended until the proximal end of the sheath 7. Thereby, the stent 2 is fixed relative to the sheath 7. To release the stent 2, the regulating portion 15 is severed to allow unrestricted movement toward the distal end direction of the sheath 7.

Next, the operation of the stent delivery system 1 in accordance with the present invention shall be described.

First, the stent 2 is mounted by placing the stent 2 on the sheath 7 so that the proximal end of the stent 2 comes into contact with the regulating portion 8. The insertion portion 5 of the endoscope 6 is inserted into the sheath 7 in this state until the position at which the curvature portion 3 extends from the distal end of the sheath 7, and is then inserted into a body cavity.

While performing observation with the endoscope 6, it is inserted until the vicinity of a constricted portion not illustrated, and furthermore, inserted with great care until the position at which the constricted portion is no longer visible. Then, the sheath 7 is extended with respect to the insertion portion 5. After the sheath 7 comes to be observable with the endoscope 6, the sheath 7 and the insertion portion 5 are drawn out to the proximal side. At this time, since the stent 2 is pressed inward in the diameter direction by the constricted portion, it is left behind at that location and placed. Then, it is confirmed with the endoscope 6 whether or not the stent 2 is placed at the desired position.

In this way, by extracting the sheath 7 and the insertion portion 5 to outside of the body, only the stent 2 is placed at the desired position of the constricted portion. Note that in the case of the position of the stent 2 being shifted, when the insertion portion 5 is in the body, the position is adjusted by inserting a predetermined treatment instrument.

Since the regulating portion 8 is provided in accordance with the stent delivery system 1, even when inserting the insertion portion 5 in the sheath 7 on which the stent 2 is disposed and inserting in a body cavity, it is possible to insert the stent 2 until a desired placement position by preventing the stent 2 from slipping off the sheath 7.

Under the present circumstances, since the curvature portion 3 is protruding from the distal end of the sheath 7, the insertion portion 5 with the relatively smaller diameter can be made to precede the sheath 7 with the relatively larger diameter. Therefore, it is possible to perform insertion while observing by curving the distal end of the insertion portion 5 in preferred direction with the curvature portion 3.

Then, as conventionally done, even without confirming the state of the stent 2 by an X-ray fluoroscope not shown, it is possible to place the stent 2 by removing it from the sheath 7 while directly observing the stent 2 via the insertion portion 5 of the endoscope 6. Accordingly, it is possible to place the stent 2 in a body cavity by observation of only the endoscope 6 without the need of excessive diametrical contraction or additional expansion of the stent 2.

Also, when inserting the stent 2 into a body cavity, it is possible to regulate movement to the proximal end side by the regulating portion 8.

Figure 4:
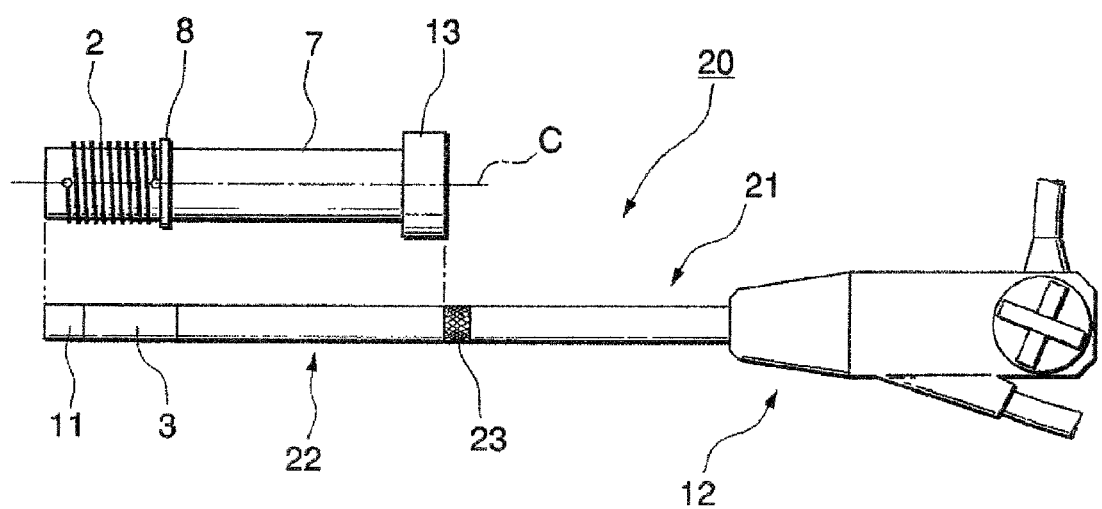
FIG. 4 is an overall schematic drawing showing the stent delivery system in accordance with the second embodiment of the present invention.

Next, a second embodiment shall be described with reference to FIG. 4.

Note that constituent elements that are the same as those of the aforementioned first embodiment are given the same reference numbers, with explanations thereof being omitted here.

The point of difference between the second embodiment and the first embodiment is that an indicator portion 23 that shows the state of alignment of the distal end of the sheath 7 and the distal end of an insertion portion 22 is provided in the insertion portion 22 of an endoscope 21 in a stent delivery system 20 in accordance with the present embodiment.

The indicator portion 23 is formed in a circular shape in the circumferential direction of the insertion portion 22, and when the distal end of the sheath 7 and the distal end of the insertion portion 22 are aligned, it is provided outside of where the proximal end of the sheath 7 is disposed.

Next, the action of the stent delivery system 20 in accordance with the present invention shall be described.

First, similarly to the first embodiment, the stent 2 is placed on the sheath 7 to fix the stent 2. The insertion portion 22 of the endoscope 21 is inserted into the sheath 7 in this state until the position at which the curvature portion 3 extends from the distal end of the sheath 7, and is inserted into the body cavity.

While performing observation with the endoscope 21, it is inserted until the vicinity of the constricted portion not illustrated, and furthermore, inserted with great care until the position at which the constricted portion is no longer visible. Then, the sheath 7 extends with respect to the insertion portion 22.

Here, when the proximal end of the grip portion 13 of the sheath 7 reaches the indicator portion 23, the distal end of the sheath 7 and the distal end of the insertion portion 22 just align. Thereafter, by a similar operation as the first embodiment, the stent 2 is placed at the desired position of the constricted portion.

Accordingly to this stent delivery system 20, it is possible to exhibit the same effect as the first embodiment. In particular, since the indicator portion 23 is provided in the sheath 7, even without observation with the endoscope 21, it is possible to align the distal end of the sheath 7 and the distal end of the insertion portion 22.

Figure 5:
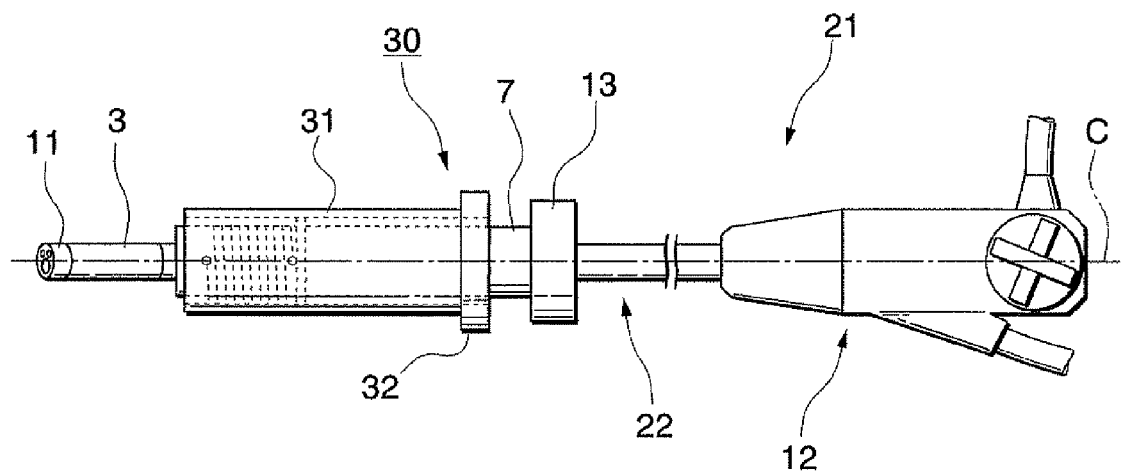
FIG. 5 is an overall schematic drawing showing the stent delivery system in accordance with the third embodiment of the present invention.

Next, the third embodiment shall be described with reference to FIG. 5.

Note that constituent elements that are the same as those of the aforementioned embodiments are given the same reference numbers, with explanations thereof being omitted here.

The point of difference between the third embodiment and the second embodiment is that a stent delivery system 30 in accordance with the present embodiment is further provided with an outer sheath 31 that is disposed in a manner to freely extend and retract with respect to the sheath 7 and additionally covers the outer side of the stent 2 in the state of the stent 2 being placed on the sheath 7.

The outer sheath 31 is formed in a cylindrical shape similarly to the sheath 7, and is formed of such a length that, in the state of being inserted over the sheath 7, when the proximal end of the outer sheath 31 abuts the grip portion 13 of the sheath 7, the stent 2 can be exposed. An outer sheath grip portion 32 that protrudes in the diameter direction similarly to the sheath 7 is provided at the proximal end of the outer sheath 31.

Next, the action of the stent delivery system 30 in accordance with the present embodiment shall be described.

First, similarly to the first embodiment, the stent 2 is placed in the sheath 7 to fix the stent 2. Next, the sheath 7 in this state is inserted in the outer sheath 31, and the distal end of the sheath 7 and the distal end of the outer sheath 31 are aligned. Then, the insertion portion 22 of the endoscope 6 is inserted until a position at which the curvature portion 3 protrudes from the distal end of the sheath 7 and the outer case 31, and is inserted into the body cavity.

While performing observation with the endoscope 6, it is inserted until the vicinity of the constricted portion not illustrated, and furthermore, inserted with great care until the position at which the constricted portion is no longer visible. Then, the sheath 7 and the outer sheath 31 are extended with respect to the insertion portion 22.

Then, the sheath 7 is advanced with respect to the insertion portion 22. Then, similarly to the second embodiment, when the proximal end of the grip portion 13 of the sheath 7 has reached the indicator portion 23, the outer sheath 31 is moved to the proximal end side with respect to the sheath 7 to expose the stent 2.

Thereafter, by performing the same operations as the first embodiment, the stent 2 is placed at the desired position of the constricted portion.

In accordance with this stent delivery system 30, since the outer sheath 31 is provided, it is possible to insert the stent 2 in a body cavity in the state of being covered with the outer sheath 31. For that reason, it is possible to favorably prevent dropping and shifting of the stent 2 during insertion. Also, it is possible to suitably prevent damage to the body cavity with the stent 2 during insertion. Moreover, by moving the outer sheath 31 with respect to the sheath 7 after insertion, the stent 2 is exposed, making it possible to remove the stent 2 from the sheath 7.

Figure 6:
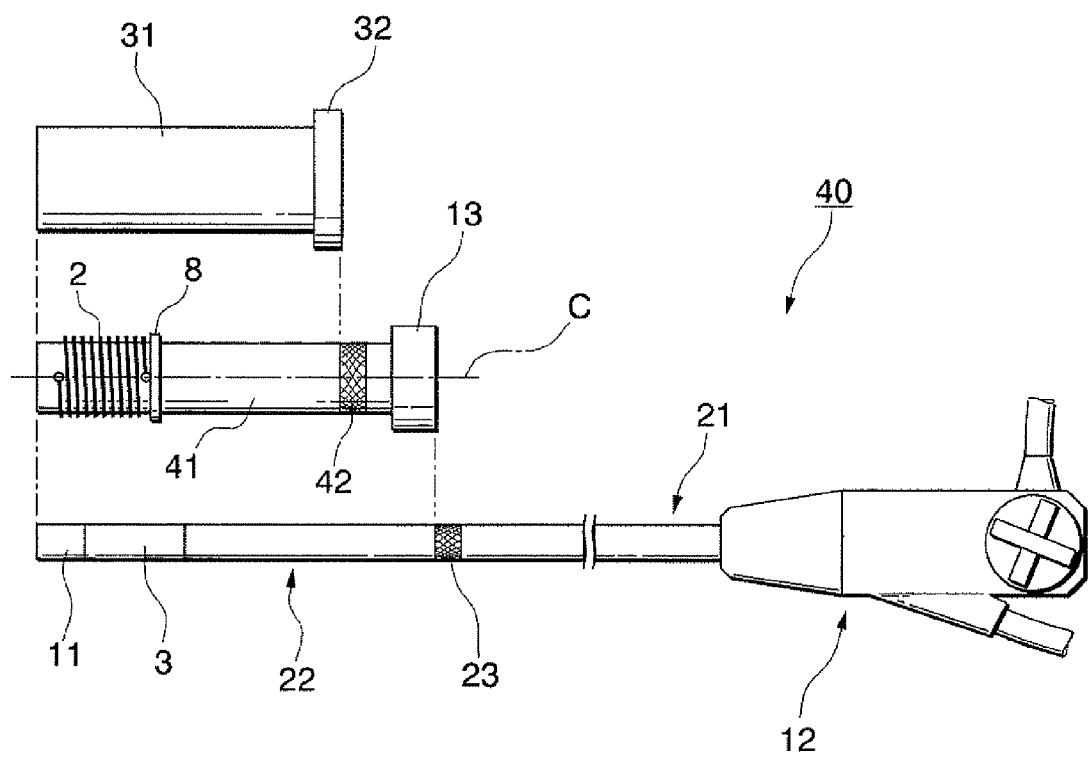
FIG. 6 is an overall schematic drawing showing the stent delivery system in accordance with the fourth embodiment of the present invention.

Next, the fourth embodiment shall be described with reference to FIG. 6.

Note that constituent elements that are the same as those of the aforementioned other embodiments are given the same reference numbers, with explanations thereof being omitted here.

The point of difference between the fourth embodiment and the third embodiment is that an outer sheath indicator portion 42 is provided that shows the state of alignment of the distal end of the outer case 31 and the distal end of a sheath 41 on the outer surface of the sheath 41 of a stent delivery system 40 in accordance with the present embodiment.

The outer sheath indicator portion 42 is formed in a circular shape similarly to the indicator portion 23 in the circumferential direction of the sheath 41, and when the distal end of the outer sheath 31 and the distal end of the sheath 41 are aligned, it is disposed on the outer surface of the position where the proximal end of the outer sheath 31 is provided.

Next, the action of the stent delivery system 40 in accordance with the present embodiment shall be provided.

First, similarly to the third embodiment, the stent 2 is placed on the sheath 41 to fix the stent 2, and moreover, the sheath 41 in this state is inserted in the outer sheath 31. At this time, the proximal end of the outer sheath grip portion 32 is aligned with the outer sheath indicator portion 42 of the sheath 41 so that the distal ends of the outer sheath 31 and the sheath 41 come into alignment. The insertion portion 22 of the endoscope 21 is inserted in the sheath 41 of this state until the position where the curvature portion 3 protrudes from the distal end of the sheath 41, and is inserted into the body cavity.

While performing observation with the endoscope 21, it is inserted until the vicinity of the constricted portion not illustrated, and furthermore, inserted with great care until the position at which the constricted portion is no longer visible. Then, the sheath 41 and the outer sheath 31 are extended with respect to the insertion portion 22.

Here, when the proximal end of the grip portion 13 of the sheath 41 reaches the indicator portion 23, the distal end of the sheath 41 and the distal end of the insertion portion 22 just align. When in this state, the outer sheath 31 is moved to the distal end side with respect to the sheath 41, thereby exposing the stent 2.

In accordance with this stent delivery system 40, since the outer sheath indicator portion 42 is provided on the sheath 41, it is possible to align the distal end of the sheath 41 and the distal end of the outer sheath 31. Accordingly, it is possible to ensure that the outer sheath 31 does not move further to the distal end side than the sheath 41, and it is possible to easily recognize the correct position of the stent 2 with the endoscope 6.

Figure 7:
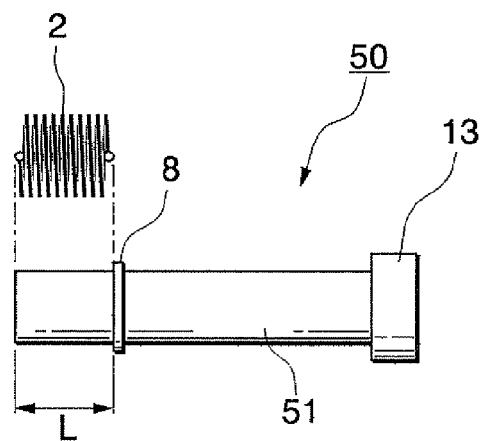
FIG. 7 is an overall schematic drawing showing the stent delivery system in accordance with the fifth embodiment of the present invention.

Next, a fifth embodiment shall be described with reference to FIG. 7.

Note that constituent elements that are the same as those of the aforementioned other embodiments are given the same reference numbers, with explanations thereof being omitted here.

The point of difference between the fifth embodiment and the first embodiment is that the regulating portion 8 of a stent delivery system 51 in accordance with the present invention is provided at a position spaced away from the distal end of the sheath 51 by a distance L that is substantially the same as the total distance of the stent 2.

In accordance with this stent delivery system 50, it is possible to substantially align the distal end of the stent 2 and the distal end of the sheath 51, and it is possible to reliably place the stent 2 at the desired position with respect to a constricted portion while confirming the distal end of the sheath 51 with the endoscope 6.

Figure 8:
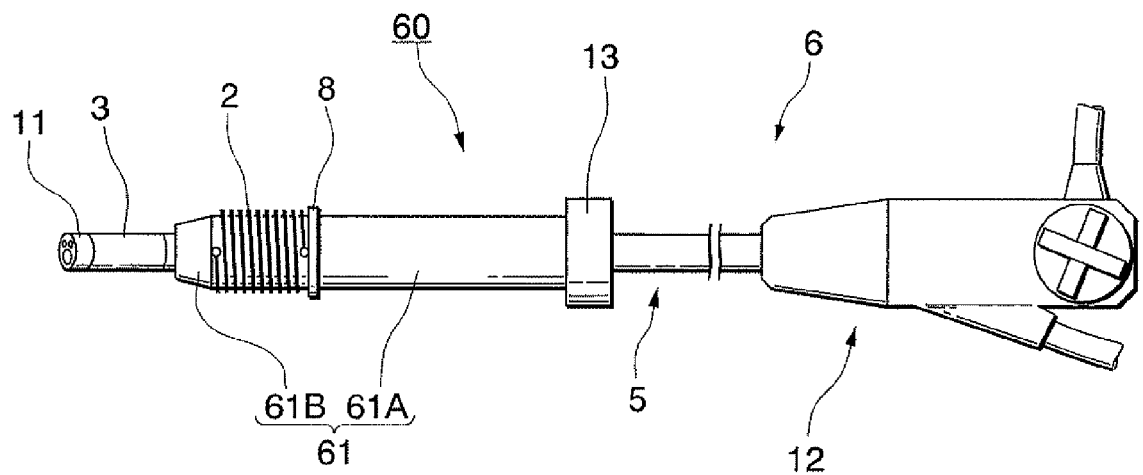
FIG. 8 is an overall schematic drawing showing the stent delivery system in accordance with the sixth embodiment of the present invention.

Next, a sixth embodiment shall be described with reference to FIG. 8.

Note that constituent elements that are the same as those of the aforementioned other embodiments are given the same reference numbers, with explanations thereof being omitted here.

The point of difference between the sixth embodiment and the first embodiment is that a sheath 61 of a stent delivery system 60 in accordance with the present invention is provided with a large diameter portion 61A that is covered by the stent 2 and a narrow diameter portion 61B having a smaller diameter than the large diameter portion 61A and disposed at the distal end of the large diameter portion 61A.

The narrow diameter portion 61B gradually contracts in diameter from the large diameter portion 61A to the distal end of the sheath 61. The stent 2 is disposed on the large diameter portion 61A. For that reason, the narrow diameter portion 61B is in a state of protruding further from the distal end of the stent 2.

The stent delivery system 60 can exhibit the same action/effect as the stent delivery system 1 in accordance with the first embodiment.

In particular, since the narrow diameter portion 61B is provided in the sheath 61, the outer diameter of the inserted material can be continuously expanded from the outer diameter of the insertion portion 5 of the endoscope 6 to the outer diameter of the large diameter portion 61A. Accordingly, it is possible to gradually open constricted portions and so it is possible to reduce the burden on the patient.

Figure 9:
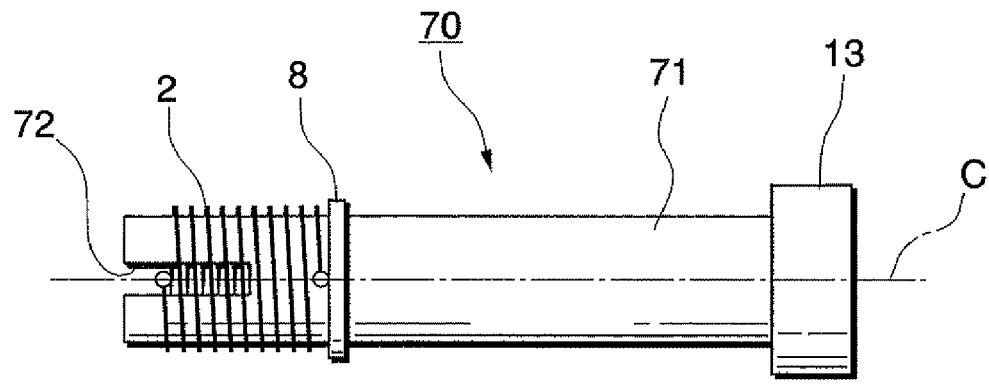
FIG. 9 is a main portion schematic drawing showing the stent delivery system in accordance with the seventh embodiment of the present invention.
Figure 10:
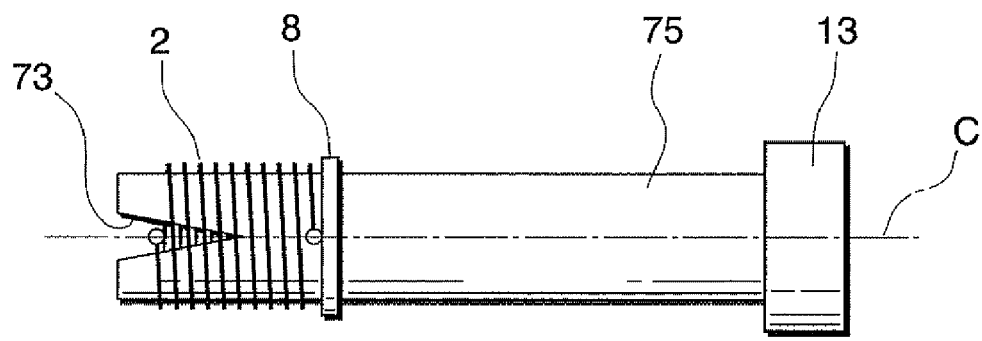
FIG. 10 is a main portion schematic drawing showing a modification example of the stent delivery system in accordance with the seventh embodiment of the present invention.

Next, a seventh embodiment shall be described with reference to FIG. 9 and FIG. 10.

Note that constituent elements that are the same as those of the aforementioned other embodiments are given the same reference numbers, with explanations thereof being omitted here.

The point of difference between the seventh embodiment and the first embodiment is that a slit (window portion) 72 that enables visual recognition of the outside of the sheath 71 by the endoscope 6 from the inside thereof is provided in the direction of the central axis line C of the sheath 71.

The slit 72 has a predetermined length and a predetermined width from the distal end of the sheath 71 to the distal end of the stent 2 in the case of the stent 2 being disposed on the sheath 71. Note that there may be more than one slit 72. Also, as shown in FIG. 10, a slit 73 may be formed to gradually narrow in width from the distal end of the sheath 75 to the proximal end side thereof.

Next, the action of a stent delivery system 70 in accordance with the present embodiment shall be described.

First, similarly to the first embodiment, the stent 2 is placed on a sheath 71 to fix the stent 2. The insertion portion 5 of the endoscope 6 is inserted into the sheath 71 in this state until the position at which the curvature portion 3 protrudes from the distal end of the sheath 71, and is inserted into the body cavity.

While performing observation with the endoscope 6, it is inserted until the vicinity of the constricted portion not illustrated, and furthermore, inserted with great care until the position at which the constricted portion is no longer visible. Then, the sheath 71 is extended with respect to the insertion portion 5.

When the distal end of the sheath 71 abuts the constricted portion, the width of the slit 72 is progressively narrowed from the distal end side of the sheath 71, causing the distal end side of the sheath 71 to be contracted in diameter. For that reason, the distal end side of the sheath 71 is smoothly inserted in the constricted portion.

Thereafter, by the operation similar to the first embodiment, the stent 2 is placed at the desired position of the constricted portion. Here, in the case of the distal end portion 11 of the endoscope 6 being put in the sheath 71, while observing the outside of the sheath 71 from the inside thereof via the slit 72, the position where the stent 2 should be placed is confirmed.

In accordance with this stent delivery system 70, since the slit 72 is provided in the sheath 71, it is possible to improve the flexibility, and in the way of the sheath 71 of the sixth embodiment, it is possible to contract the diameter of the distal end side of the sheath 71 in the constricted portion. Also, even in the state of the insertion portion 5 being inserted in the sheath 71, it is possible to readily observe the outside of the sheath 71 from the inside thereof via the slit 72.

Next, an eighth embodiment shall be described with reference to FIG. 11 to FIG. 13B.

Note that constituent elements that are the same as those of the aforementioned other embodiments are given the same reference numbers, with explanations thereof being omitted here.

The point of difference between the eighth embodiment and the seventh embodiment is that a plurality of window portions 82 is arranged along the direction of the central axis line C instead of the slit 72 on a sheath 81 of a stent delivery system 80 in accordance with the present embodiment.

Figure 11:
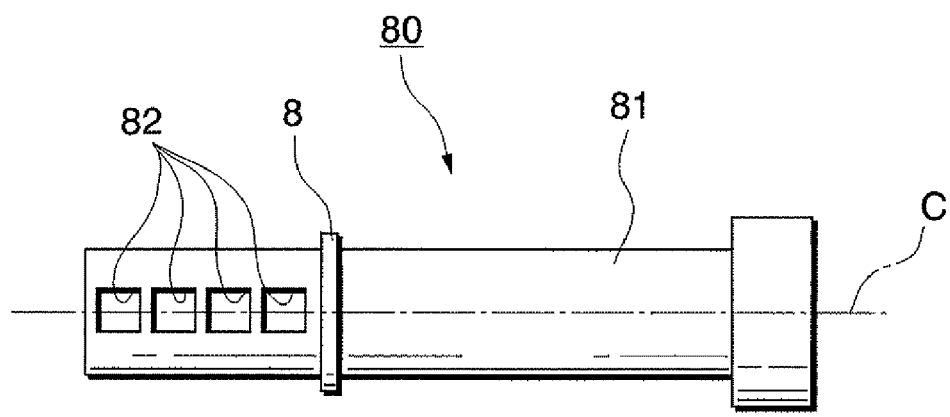
FIG. 11 is a main portion schematic drawing showing the stent delivery system in accordance with the eighth embodiment of the present invention.
Figure 12A:
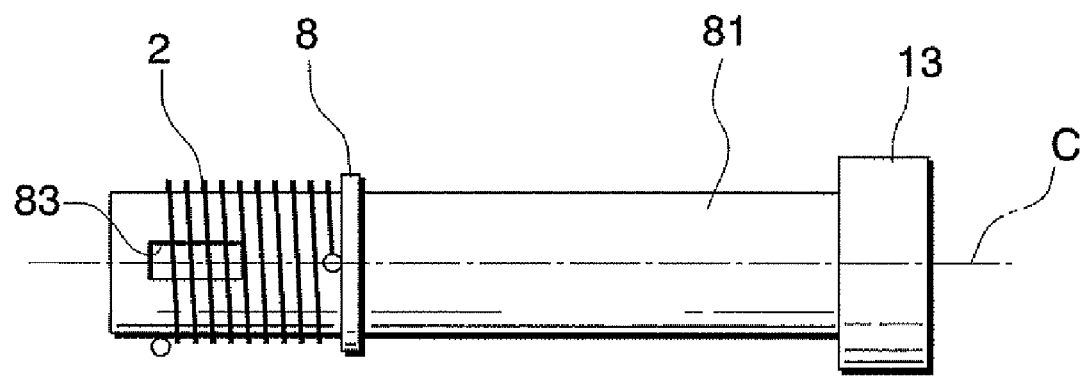
FIG. 12A is a main portion schematic drawing showing the visual field of the endoscope in a modification example of the stent delivery system in accordance with the eighth embodiment of the present invention.

Each window portion 82 is, as shown in FIG. 11, rectangular, but is not limited to being rectangular, and may be round, elliptical, or another multangular shape. Also, there may be a single, long window portion 83 in the direction of the central axis line C as shown in FIG. 12A without the need of being a plurality of windows.

Figure 12B:
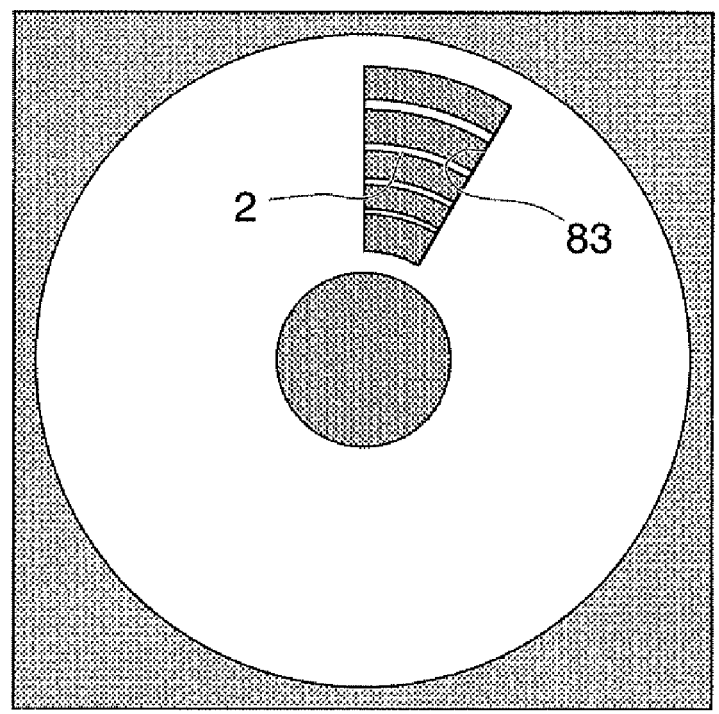
FIG. 12B is an explanatory drawing showing the visual field of the endoscope in a modification example of the stent delivery system in accordance with the eighth embodiment of the present invention.
Figure 13A:
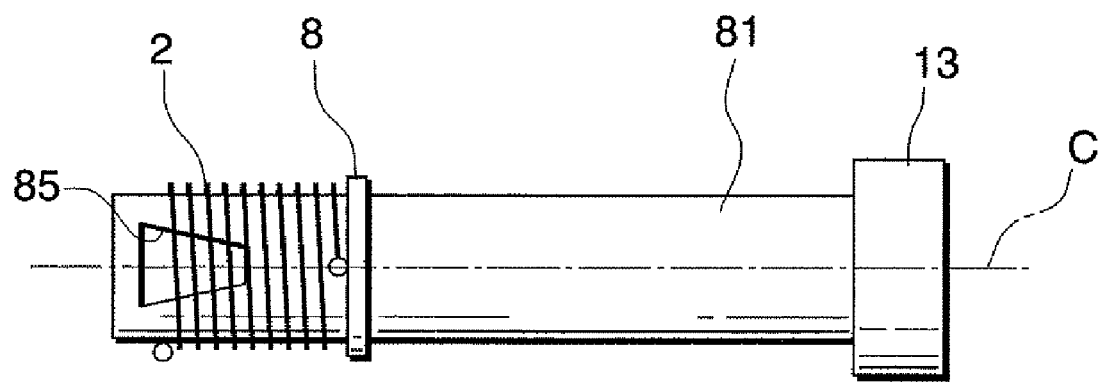
FIG. 13A is a main portion schematic drawing showing the visual field of the endoscope in a modification example of the stent delivery system in accordance with the eighth embodiment of the present invention.
Figure 13B:
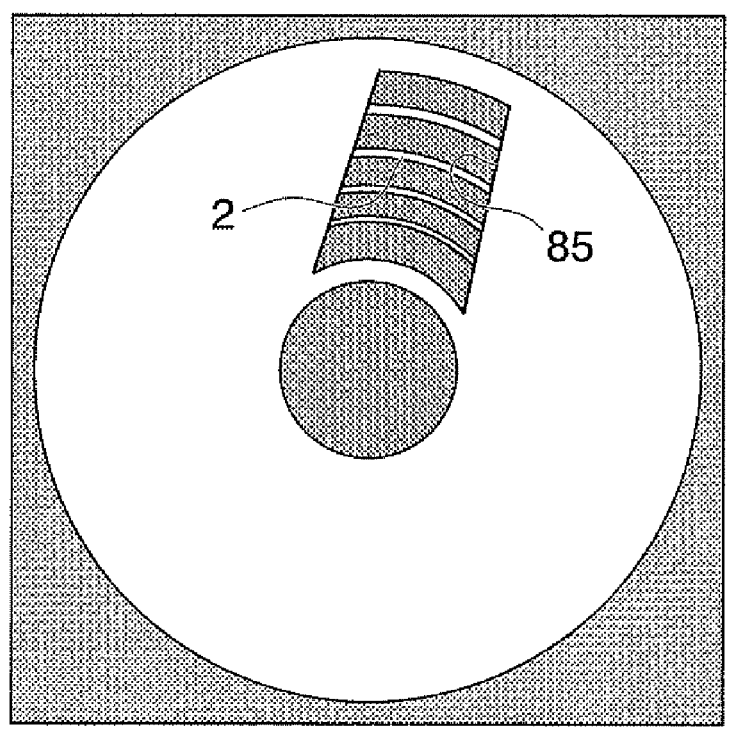
FIG. 13B is an explanatory drawing showing the visual field of the endoscope in a modification example of the stent delivery system in accordance with the eighth embodiment of the present invention.

In this case, as shown in FIG. 12B, when observing from the endoscope, the window portion 83 appears to be narrowed in width from the circumferential edge side to the central portion side of the visual field. For that reason, the distal end side of the stent 2 can be somewhat harder to see than the proximal end side thereof. Therefore, as shown in FIG. 13A, the width of the distal end side is made greater than the width of the proximal end side. In the case of a window portion 85 with a trapezoidal shape in which the width progressively changes in the direction of the central axis line C, as shown in FIG. 13B, the width appears to conversely widen along the direction from the circumferential edge side to the central portion side of the visual field. For that reason, the distal end side of the stent 2 can be more easily seen than the proximal end side thereof.

In accordance with this stent delivery system 80, by observing through the window portion 82 instead of the slit 72, it is possible to exhibit the same action/effect as the stent delivery system 70 in accordance with the seventh embodiment.

Figure 14:
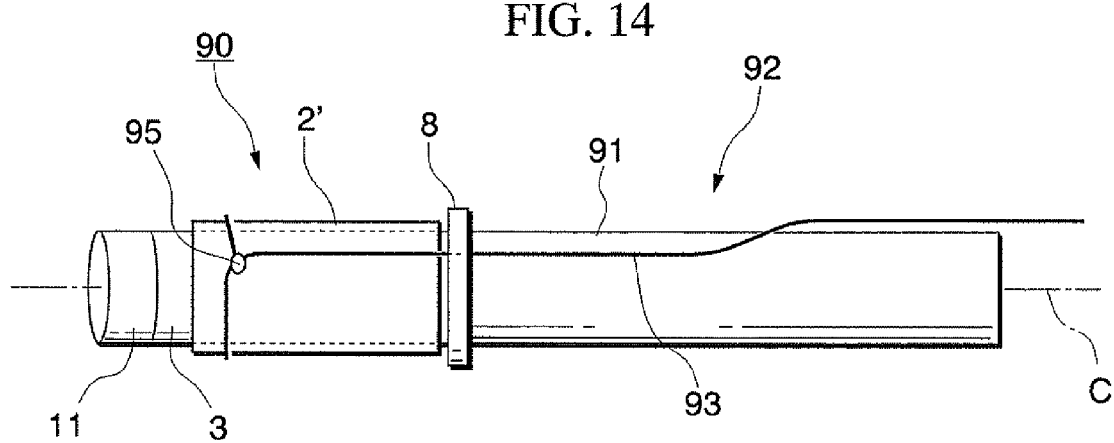
FIG. 14 is a main portion schematic drawing showing the stent delivery system in accordance with the ninth embodiment of the present invention.

Next, a ninth embodiment shall be described with reference to FIG. 14 to FIG. 16.

Note that constituent elements that are the same as those of the aforementioned other embodiments are given the same reference numbers, with explanations thereof being omitted here.

The point of difference between the ninth embodiment and the first embodiment is that a stent delivery system 90 in accordance with the present embodiment is provided with an endoscope 92 that has an insertion portion 91 that is inserted in a body cavity with a stent 2' disposed thereon by being placed on the outside surface of the distal end side thereof, and a regulating portion 8 that regulates the relative movement of the stent 2' with respect to the proximal end side of the insertion portion 91.

The stent delivery system 90 in accordance with the present embodiment does not have a sheath 7 as in the stent delivery system 1 in accordance with the first embodiment, and thus the stent 2' is directly inserted on the insertion portion 91.

The regulating portion 8 is provided at a position spaced by a predetermined distance from the distal end of the insertion portion 91 and protrudes greatly from the outer surface of the insertion portion 91 outward in the radial direction further than the outer diameter of the stent 2'. A thread 93 is wound approximately once around the outer surface of the distal end portion of the stent 2', and a ball portion 95 is formed by the distal end of the thread 93 being heat welded to a middle portion of the thread 93. Here, the adhesion strength of the thread is adjusted so as to be less than the tensile strength of the thread 93. The thread 93 is, for example, dyed red so as to be a color that is observable from the insertion portion 91.

Figure 15:
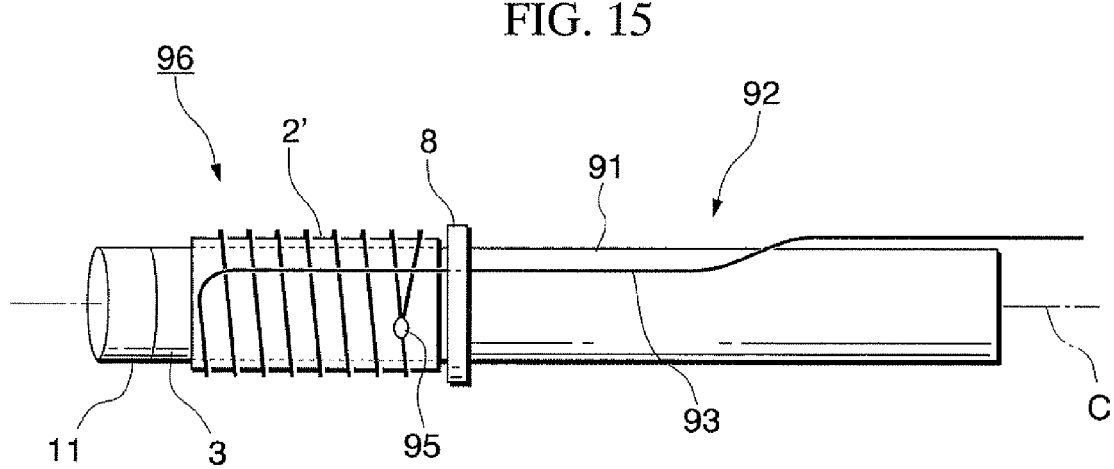
FIG. 15 is a main portion schematic drawing showing a modification example of the stent delivery system in accordance with the ninth embodiment of the present invention.

Now, as shown in FIG. 15, a stent delivery system 96 is also possible in which the thread 93 is wound in a spiral on the outer surface from the proximal end side of the stent 21 to the distal end side thereof, and moreover folded back from the distal end side and disposed on the already wound thread 93 toward the proximal end side of the insertion portion 91.

In this case as well, a ball portion 95 is formed by the distal end of the thread 93 being heat welded to a middle portion of the thread 93 by the same strength as described above.

Figure 16:
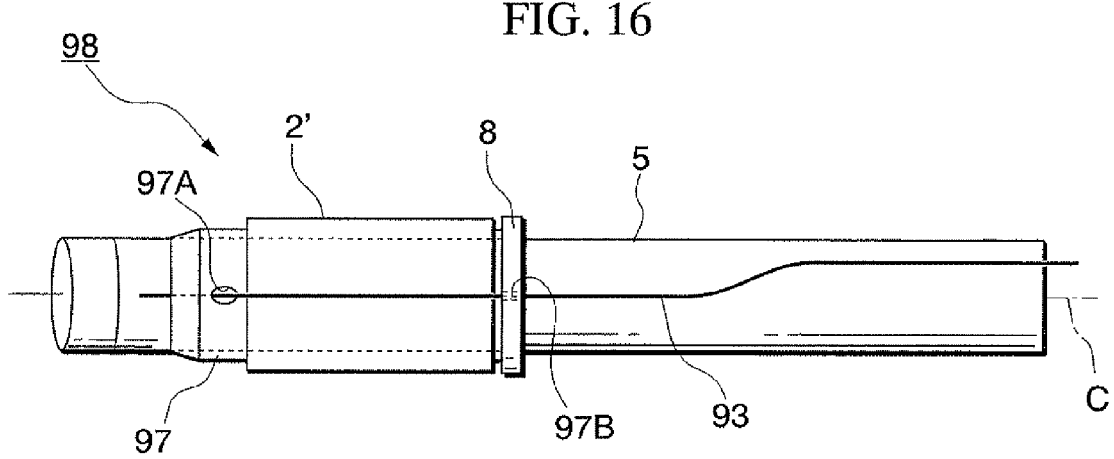
FIG. 16 is a main portion schematic drawing showing a modification example of the stent delivery system in accordance with the ninth embodiment of the present invention.

Also, as shown in FIG. 16, there may also be a stent delivery system 98 in which a tube portion 97, which is externally fitted in a freely detachable manner on the insertion portion 5 and on which the stent 2' is disposed on the outer surface thereof, is provided and the regulating portion 8 is provided on the proximal end of the tube portion 97 instead of being provided on the insertion portion 91. A first through hole 97A is provided on the outside surface of the distal end side of the tube portion 97 that is exposed from the stent 2, in the state of the proximal end of the stent 2' being abutted against the regulating portion 8. The outer diameter of the distal end of the tube portion 97 progressively contracts in diameter so as to be the same as the outer diameter of the insertion portion 5. Then, the distal end of the thread 93 is fixed by being press fitted between the distal end side of the insertion portion 5 and the tube portion 97, passed through the first through hole 97A from the inside to the outside, directed toward the proximal end side on the outer surface of the stent 2' along the central axis line C, passed through a second through hole 97B that is provided in the regulating portion 8 to head toward the proximal end side of the insertion portion 5. The stent 2' is thus disposed by releasing the thread 93 from the first through hole 97A by pulling with a force not less than the press fitting force.

Next, the action of the stent delivery system 90 in accordance with the present embodiment shall be described.

First, the stent 2' is mounted by placing the stent 2' on the insertion portion 91 so that the proximal end of the stent 2' abuts the regulating portion 8.

While performing observation with the endoscope, it is inserted until the vicinity of the constricted portion not illustrated, and furthermore, inserted with great care until the position at which the constricted portion is no longer visible. Then, the thread 93 is pulled toward the proximal side. At this time, when the tensile force of the thread 93 exceeds the fixing force of the thread 93 at the ball portion 95, the distal end of the thread 93 separates from the ball portion 95. By pulling and removing the thread 93, the insertion portion 91 is drawn to the proximal side. At this time, since the stent 2' is pressed inward in the radial direction by the constricted portion, the stent 2' is placed by being left behind at that location. Thereafter, whether the stent 2' has been placed at the desired position is visibly confirmed with the endoscope 6.

In this way, by extracting the insertion portion 91 to outside of the body, only the stent 2' is placed at the desired position of the constricted portion. Note that in the case of the position of the stent 2' being shifted, when the insertion portion 5 is in the body, the position is adjusted by inserting a predetermined treatment instrument.

In accordance with this stent delivery system 90, it is possible to reliably place the stent 2' in a body even without using a sheath.

Next, a tenth embodiment shall be described with reference to FIG. 17 to FIG. 19.

Note that constituent elements that are the same as those of the aforementioned first embodiment are given the same reference numbers, with explanations thereof being omitted here.

Figure 17:
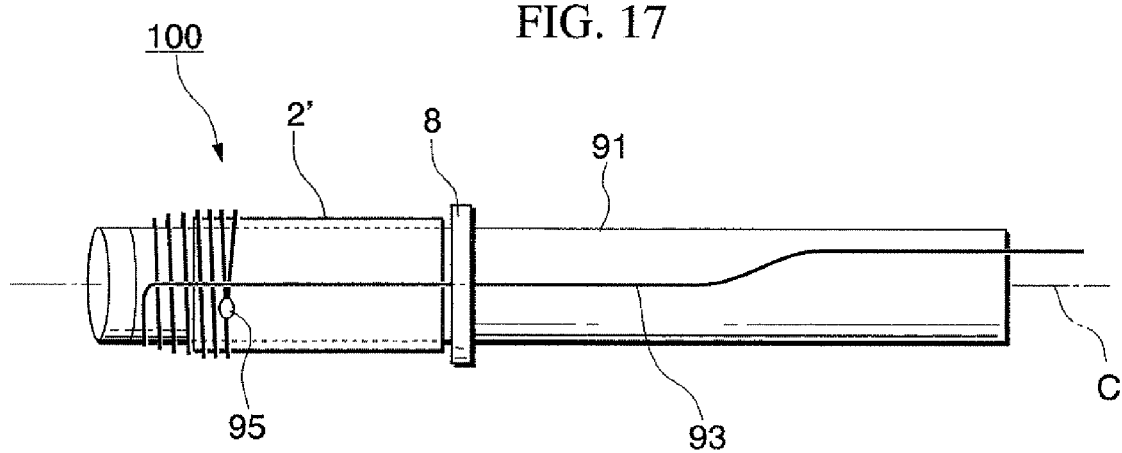
FIG. 17 is a main portion schematic drawing showing the stent delivery system in accordance with the tenth embodiment of the present invention.

The point of difference between the tenth embodiment and the ninth embodiment is that a thread (diameter adjustment portion) 93 of a stent delivery system 100 in accordance with the present embodiment is wound so that the outer diameter of at least the distal end side of the stent 2' that is disposed on the insertion portion 91 gradually approaches the outer diameter of the insertion portion 91, as shown in FIG. 17.

Since the outer diameter of the stent 2' is greater than the outer diameter of the insertion portion 91, when the stent 2' is placed on the insertion portion 91, a step arises between the insertion portion 91 and the stent 2'. Accordingly, in order to eliminate this step, the thread 93 is fastened by being wound to extend from the distal end side of the stent 2' to the outer surface of the insertion portion 91, thereby gently altering the outer diameter. A ball portion 95 is formed by the distal end of the thread 93 being heat welded to a middle portion of the thread 93.

Figure 18:
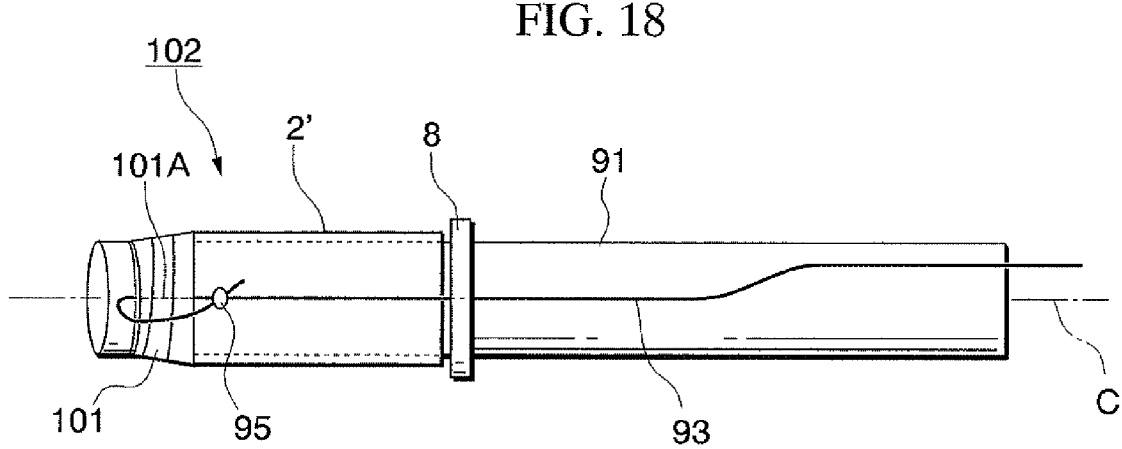
FIG. 18 is a main portion schematic drawing showing a modification example of the stent delivery system in accordance with the tenth embodiment of the present invention.

Note that, as shown in FIG. 18, a stent delivery system 102 is also possible in which a belt-like sheet (diameter adjustment portion) 101 is wound on the distal end side of the stent 2' instead of the thread 93. A perforated line 101A is provided in the width direction of the belt-like sheet 101. The distal end side of the thread 93 is press fitted from the proximal end side between the belt-like sheet 101 and the insertion portion 91, and then folded back over the outer surface of the belt-like sheet 101 toward the proximal end side to be heat welded at the ball portion 95. That is, the thread 93 does not adjust the outer diameter, and is used when removing the stent 2' that is fixed by the belt-like sheet 101 from the insertion portion 91. When doing so, when the thread 93 is pulled toward the proximal side, the belt-like sheet 101 is severed along the perforated line 101A to enable the stent 2' to be released from the insertion portion 91.

Figure 19:
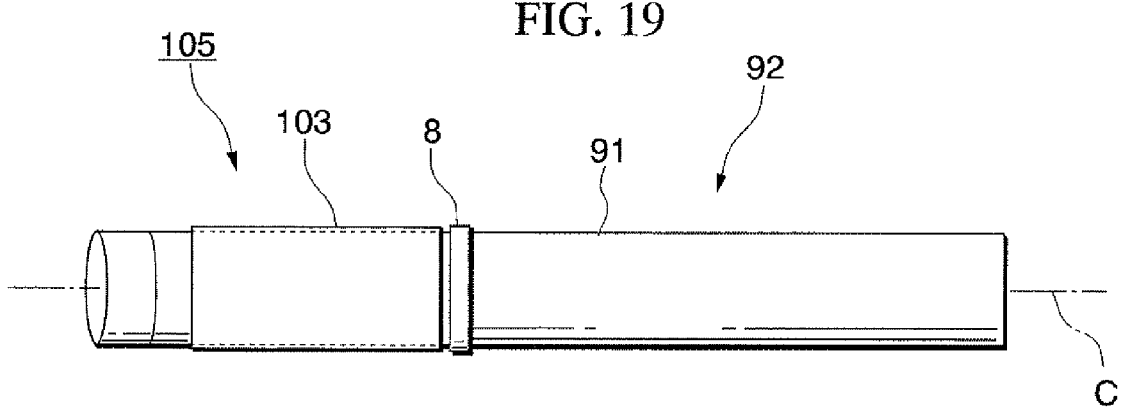
FIG. 19 is a main portion schematic drawing showing a modification example of the stent delivery system in accordance with the tenth embodiment of the present invention.

Note that, as shown in FIG. 19, a stent delivery system 105 is also possible in which a stent 103 with an outer diameter approximately the same as the outer diameter of the insertion portion 91 is disposed by being placed on the insertion portion 91, instead of using the thread 93 and the belt-like sheet 101.

In accordance with this stent delivery system 100, when inserting the stent 2', it is possible to substantially eliminate the step between the distal end of the stent 2' and the outer circumference of the insertion portion 91, and so it is possible to smoothly perform insertion of the insertion portion 91.

Figure 20A:
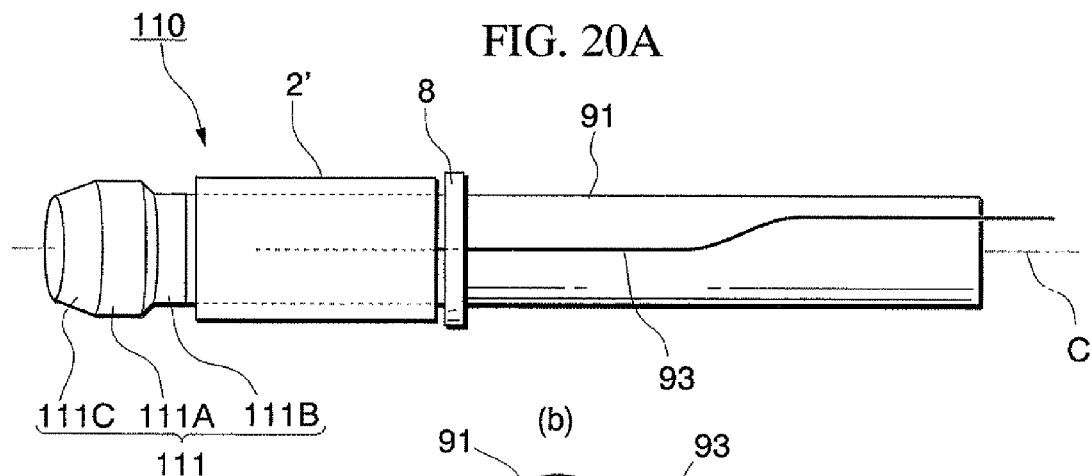
FIG. 20A is a main portion schematic drawing showing the stent delivery system in accordance with the eleventh embodiment of the present invention.
Figure 20B:
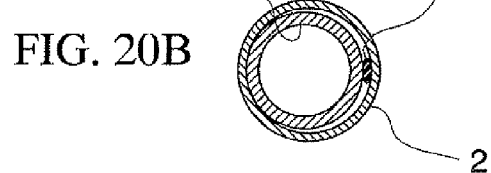
FIG. 20B is a main portion schematic drawing showing the stent delivery system in accordance with the eleventh embodiment of the present invention.

Next, an eleventh embodiment shall be described with reference to FIG. 20A, FIG. 20B and FIG. 21.

Note that constituent elements that are the same as those of the aforementioned other embodiments are given the same reference numbers, with explanations thereof being omitted here.

The point of difference between the eleventh embodiment and the ninth embodiment is that a distal end cap 111 is freely detachably mounted on the distal end of the insertion portion 91 of a stent delivery system 110 in accordance with the present embodiment.

The distal end cap 111 includes a protrusion portion 111A, a connection portion 111B to the distal end of the insertion portion 91, and a small diameter portion 111C. The outer diameter of the protrusion portion 111A is larger than the outer diameter of insertion portion 91 and smaller than the inner diameter of the stent 2'. The connection portion 111B is disposed on the proximal end side of the protrusion portion 111A. The small diameter portion 111C is disposed on the distal end side of the protrusion portion 111A and the distal end outer diameter of the small diameter portion 111C is smaller than the proximal end side of the insertion portion 91. The connection portion 111B and the small diameter portion 111C interpose the protrusion portion 111A therebetween. The outer diameter of the small diameter portion 111C progressively contracts in diameter from the side of the protrudeion portion 111A to the distal end.

A thread 93 that is press fitted between the insertion portion 91 and the stent 2' increases the friction between the insertion portion 91 and the stent 2', whereby the stent 2' is fixed to the insertion portion 91.

When the thread 93 has been pulled toward the proximal end side of the insertion portion 91, a gap is created between the insertion portion 91 and the stent 2' that causes the friction to decrease. Thereby, the stent 2' enters a state of being movable to the distal end side.

In accordance with this stent delivery system 110, by reducing the resistance of the insertion portion 91, insertion can be smoothly performed.

Figure 21:
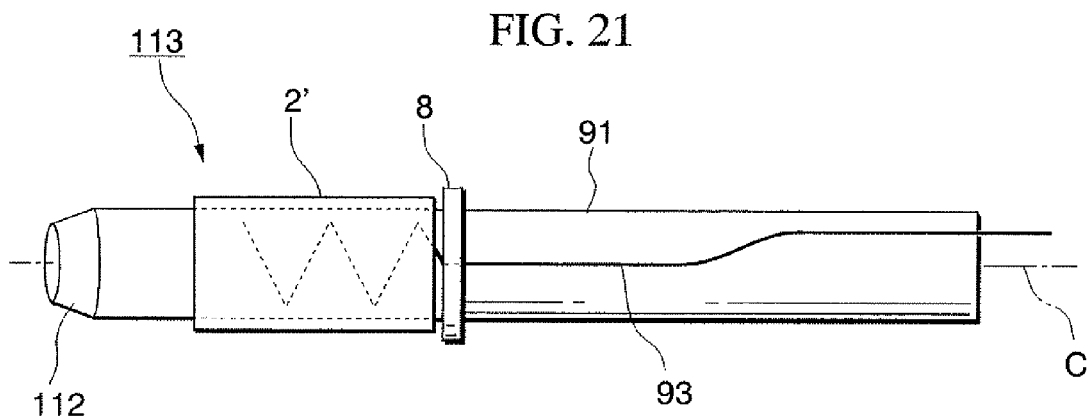
FIG. 21 is a main portion schematic drawing showing a modification example of the stent delivery system in accordance with the eleventh embodiment of the present invention.

Note that as shown in FIG. 21, there may also be a stent delivery system 113 in which a small diameter portion 112 with no protrusion portion is provided at the distal end of the insertion portion 91. In this case, by press fitting the thread 93 in a zigzag manner, the stent 2' is fixed by increasing the friction further.

While preferred embodiments of the invention have been described and illustrated above, it should be understood that these are exemplary of the invention and are not to be considered as limiting. Additions, omissions, substitutions, and other modifications can be made without departing from the spirit or scope of the present invention.

Figure 22:
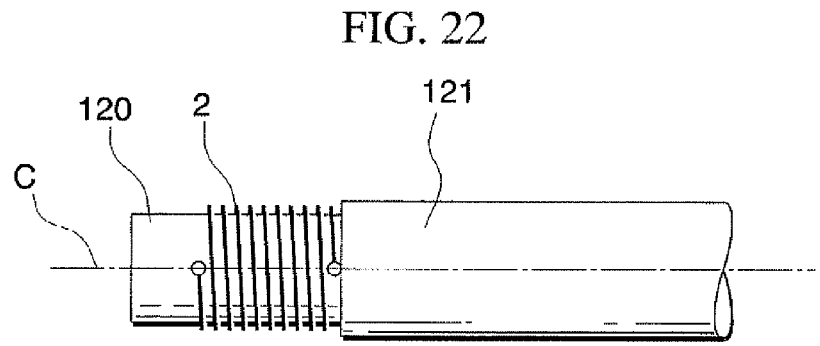
FIG. 22 is a main portion schematic drawing showing a modification example of the stent delivery system in accordance with the first embodiment of the present invention.

For example, in the seventh and eight embodiments, the slit 72 or the window portions 82 were provided to enable visibility from the inside to the outside of the sheaths 71 and 81. However, the slit 72 and the window portions 82 may be provided at the distal end of the outer sheath 31 in the third and fourth embodiments. Also, a portion where the stent 2 is disposed may be a sheath formed of a transparent material instead of the slit 72 or the window portions 82. Also, as shown in FIG. 22, it is possible to adopt a constitution in which a stent 2 is placed on the distal end side of a sheath 120, and a sheath large diameter portion 121 with a larger outer diameter than the stent 2 is disposed further to the proximal end side than the position where the stent 2 is disposed, so that the sheath large diameter portion 121 regulates as a regulating portion the relative movement of the stent 2 toward the proximal end side of the sheath 120. In this case, since the sheath 120 and the regulating portion are integrated, it is possible to construct a low-cost system. Also, it is possible to favorably prevent the regulating portion from slipping off the sheath.

Moreover, as shown in FIG. 23A, a sheath 125 may be provided with a distal end portion 125A and a proximal end portion 125B with no slits 125a. The distal end portion 125A has flexibility compliant with the curving operation of the insertion portion 5 by having slits 125a. In this case, it is preferable that the stent 2 also has similar flexibility, and may also have flexibility that is compliant with the curving of the insertion portion 5. In this case, as shown in FIG. 23B, it is possible to suitably curve the distal end portion 125A.

For that reason, it is possible to favorably improve the curving operation.

Also, as shown in FIG. 24A and FIG. 24B, a sheath 126 may be provided with a distal end portion 126A that has flexibility compliant with the curving operation of the insertion portion 5 and a proximal end portion 126B that is more rigid than the distal end portion 126A. For example, Gore-Tex (registered trademark), nylon, PTFE and the like may be used as the component material of the distal end portion 126A. In this case, as shown in FIG. 24B, it is possible to favorably curve the distal end portion 126A.

Also, as shown in FIG. 25A and FIG. 25B, a sheath 127 may be provided with a thin-walled distal end portion 127A and a proximal end portion 127B with a thicker wall thickness than the distal end portion 127A. In this case as well, as shown in FIG. 25B, it is possible to favorably curve the distal end portion 127A.

Also, as shown in FIG. 26A and FIG. 26B, a sheath 128 may be provided with a distal end portion 128A and a proximal end portion 128B. The distal end portion 128A has a plurality of holes 128a instead of slits 125a, while the proximal end portion 128B has no holes 128a. In this case as well, it is possible to favorably curve the distal end portion 127A as shown in FIG. 26B.

Figure 27:
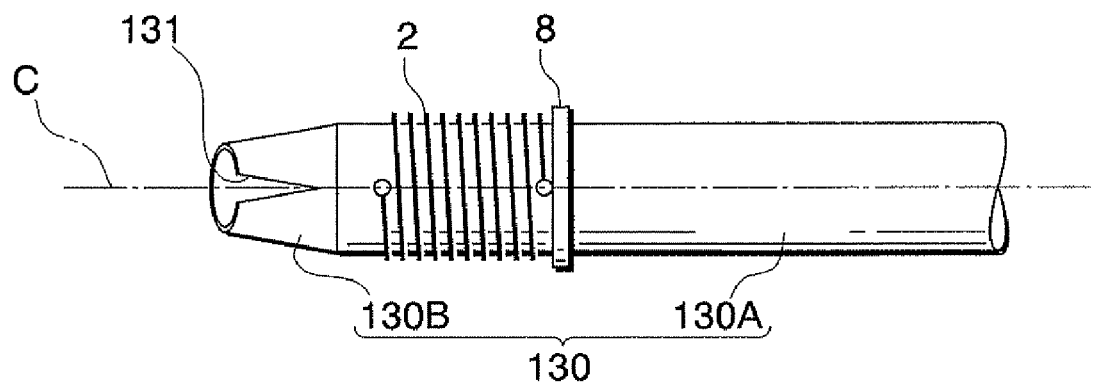
FIG. 27 is a main portion schematic drawing showing a modification example of the stent delivery system in accordance with the sixth embodiment of the present invention.

Also, as shown in FIG. 27, a sheath 130 may be provided with a large diameter portion 130A on which a stent 2 is placed and a narrow diameter portion 130B that is disposed at the distal end of the large diameter portion 130A. The outer diameter of the narrow diameter portion 130B progressively contracts toward the distal end, and the inner diameter of the distal end thereof is approximately the same as or smaller than the outer diameter of the insertion portion 5. In this case, a slit 131 is provided from the distal end of the narrow diameter portion 130B to the proximal end side. When inserting the insertion portion 5 in the sheath 130, the slit 131 expands. Since the inner diameter of the narrow diameter portion 130B thereby widens, it is possible to insert the insertion portion 5. Then, since the slit 131 is in close contact with the insertion portion 5, a step between the insertion portion 5 and the distal end of the sheath 130 is eliminated so that insertion can smoothly be performed.

Figure 28:
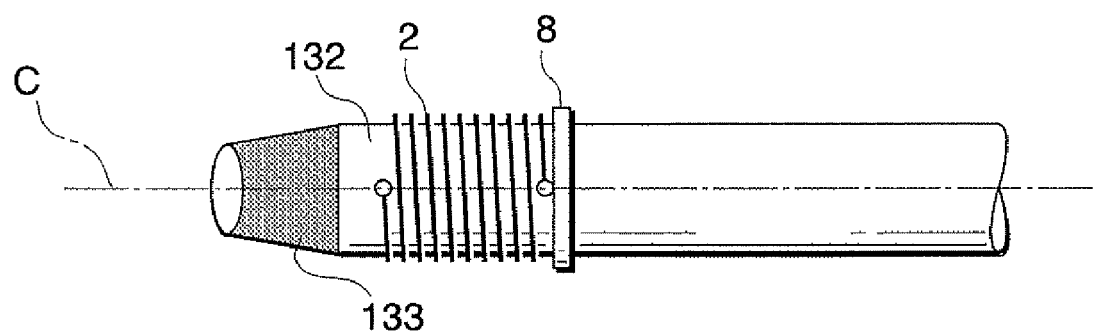
FIG. 28 is a main portion schematic drawing showing a modification example of the stent delivery system in accordance with the first embodiment of the present invention.

Also, as shown in FIG. 28, a flexible portion 133 that is formed of synthetic rubber latex, silicone rubber, nylon or the like that is more flexible than the member that forms the sheath 132 may be connected to the distal end of the sheath 132. In this case, when making contact with body cavity tissue, it is possible to make contact more flexibly than the case of this portion being rigid, and so it is possible to more readily perform expansion of the constricted portion.

Figure 29:
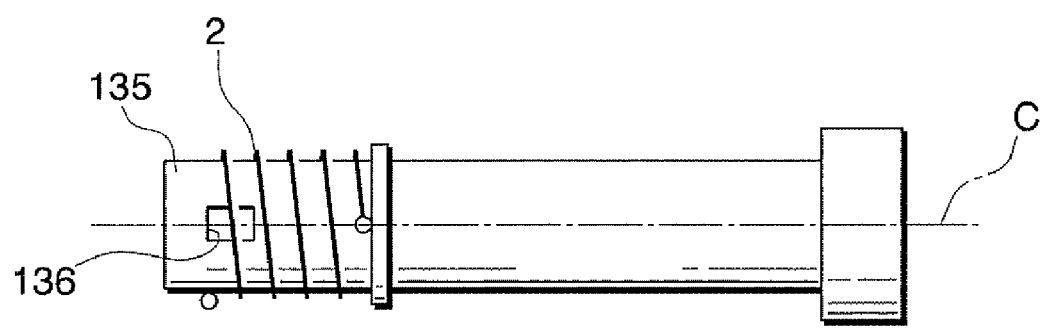
FIG. 29 is a main portion schematic drawing showing a modification example of the stent delivery system in accordance with the eighth embodiment of the present invention.

Also, as shown in FIG. 29, a window portion 136 may be disposed at a position of the sheath 135 where at least a portion of the most distal end of the stent 2 is viewable by the endoscope 6. Thereby, at least a portion of the most distal end of the stent 2 is visible by the endoscope 6, and so placement of the stent 2 can be safely performed.

In accordance with the first aspect of the stent delivery system of the present invention, the arrangement of the regulating portion allows the insertion of a stent to the desired placement position while preventing the stent from slipping off the sheath even when the insertion portion is inserted into the sheath on which a stent is placed and inserted into a body cavity. Also, it is possible to make the insertion portion with a relatively small diameter precede the sheath with a relatively large diameter.

In accordance with the second aspect of the stent delivery system of the present invention, it is possible to readily confirm whether or not the distal end of the sheath and the distal end of the insertion portion are aligned.

In accordance with the third aspect of the stent delivery system of the present invention, it is possible to insert a stent in a body cavity in the state of being covered by the outer sheath. Also, by moving the outer sheath with respect to the sheath, it is possible to remove the stent from the sheath by exposing the stent.

In accordance with the forth aspect of the stent delivery system of the present invention, it is possible to regulate the forward movement of the stent between the sheath and the line.

In accordance with the fifth aspect of the stent delivery system of the present invention, when inserting the sheath in a constricted portion, since the sheath is inserted from the narrow diameter portion thereof, it is possible to slowly expand the constricted portion until the insertion of the large diameter portion, and so it is possible to reduce the burden on the patient.

In accordance with the sixth and seventh aspect of the stent delivery system of the present invention, it is possible to readily observe the outside of the sheath from the inside via the window portion even in the state of the insertion portion being inserted in the sheath.

In accordance with the eighth aspect of the stent delivery system of the present invention, it is possible to protrude the curvature portion from the sheath and thus it is possible to insert the distal end of the insertion portion while curving it in preferred direction during observation.

In accordance with the ninth aspect of the stent delivery system of the present invention, it is possible to allow the construction of a low-cost system since the regulating portion and the sheath are integrally formed. Also, it is possible to suitably prevent the regulating portion from falling off the sheath.

In accordance with the tenth aspect of the stent delivery system of the present invention, it is possible to smoothly perform a curving operation of the endoscope even when a stent is disposed.

In accordance with the tenth aspect of the stent delivery system of the present invention, it is possible to prevent the occurrence of a step between the narrow diameter portion and the endoscope due to the slit, and so makes it possible to smoothly perform insertion.

In accordance with the twelfth aspect of the stent delivery system of the present invention, since the portion in contact with tissue is flexible, it is possible to make a soft contact with tissue.

In accordance with the thirteenth aspect of the stent delivery system of the present invention, since at least a portion of the distal end of the stent is visually recognized, it is possible to safely perform stent placement.

In accordance with the fourteenth aspect of the stent delivery system of the present invention, it is possible to place a stent on the insertion portion, and moreover since a regulating portion is provided, even when the stent is placed on the insertion portion and inserted in a body cavity, it is possible to insert the stent at the desired placement location while preventing the stent from slipping off the insertion portion.

In accordance with the present invention, it is possible to place a stent in a body cavity by observation with an endoscope without the need of excessive diametrical contraction and additional expansion of the stent.

What is claimed is:

1. A stent delivery system for supplying a stent to a body cavity, the stent delivery system comprising:
    an endoscope comprising an insertion portion that is adapted to be inserted into the body cavity;
    a sheath defining a lumen within which the insertion portion of the endoscope is removably inserted, the sheath being configured for the stent to be arranged on the outer surface of the distal end of the sheath; and
    a regulating portion configured to regulate the relative movement of the stent to the proximal end side of the sheath;
    wherein the sheath is configured to be movable with respect to the endoscope and the insertion portion, and the sheath is formed of a length that allows the distal end of the insertion portion that is inserted in the sheath to protrude from the distal end of the sheath.

2. The stent delivery system in accordance with claim 1, further comprising:
    an indictor portion that shows the state of alignment of the distal end of the sheath and the distal end of the insertion portion on the insertion portion.

3. The stent delivery system in accordance with claim 1, further comprising:
    an outer sheath that is disposed in a manner to freely extend and retract with respect to the sheath and additionally covers the outer side of the stent in the state of the stent being placed on the sheath.

4. The stent delivery system in accordance with claim 1, wherein the regulating portion is provided with a line, with at least a portion of the line being connected to the distal end side of the sheath in the vicinity of the stent in the state of being in contact with the stent.

5. The stent delivery system in accordance with claim 1, wherein the sheath comprises a large diameter portion that is covered by the stent and a narrow diameter portion having a smaller diameter than the large diameter portion and disposed at the distal end of the large diameter portion.

6. The stent delivery system in accordance with claim 1, wherein a window portion that enables visual recognition by the endoscope of the outside of the sheath from the inside thereof is provided on the distal end side of the sheath.

7. The stent delivery system in accordance with claim 6, wherein the window portion is constituted by the distal end side of the sheath being formed of a transparent material.

8. The stent delivery system in accordance with claim 1, wherein a curvature portion is disposed on the distal end side of the insertion portion, and the sheath is formed of a length that allows the curvature portion to protrude from the distal end thereof.

9. The stent delivery system in accordance with claim 1, wherein a sheath large diameter portion that is larger than the outer diameter of the stent is provided further to the proximal end side of the sheath than the position where the stent is placed, with the sheath large diameter portion serving as the regulating portion.

10. The stent delivery system in accordance with claim 8, wherein at least a portion of the distal end side of the sheath curves in compliance with the curving of the curvature portion.

11. The stent delivery system in accordance with claim 5, wherein the inner diameter of at least a portion of the narrow diameter portion is formed approximately the same as the outer diameter of the endoscope or smaller than the outer diameter of the endoscope; and a slit is provided in a portion of the narrow diameter portion.

12. The stent delivery system in accordance with claim 1, wherein a flexible portion having a member that is more flexible than the member that constitutes the sheath is disposed at the distal end of the sheath.

13. The stent delivery system in accordance with claim 6, wherein the window portion is disposed at a position of the sheath where at least a portion of the most distal end of the stent that is disposed by placement on the sheath is visually recognizable.

14. A stent delivery system for supplying a stent to a body cavity, comprising:
   an endoscope that has an insertion portion that is inserted into a body cavity, and disposed with the stent placed on the outer surface of the distal end side thereof;
   a regulating portion that regulates the relative movement of the stent to the proximal end side of the insertion portion; and
   a thread wound around the stent to hold and release the stent,
   wherein the thread has a ball portion which is formed by attaching a distal end of the thread on a middle portion of the thread to be broken by tensile force of the thread so as to release the stent.

15. The stent delivery system in accordance with claim 14, wherein a curvature portion is disposed on the distal end side of the insertion portion, and the stent is formed to be capable of curving in compliance with the curving of the curvature portion.

16. The stent delivery system in accordance with claim 14, further comprising:
   a diameter adjustment portion that makes the outer diameter of at least the distal end side of the stent that is disposed on the insertion portion gradually approach the outer diameter of the insertion portion.

17. The stent delivery system in accordance with claim 14, wherein a small diameter portion in which the outer diameter of at least a portion thereof is smaller than the proximal end side of the insertion portion is disposed at the distal end of the insertion portion.

* * * * *